(12) United States Patent
Tall

(10) Patent No.: US 6,773,893 B1
(45) Date of Patent: Aug. 10, 2004

(54) HUMAN ABC1 PROMOTER AND ASSAYS BASED THEREON

(75) Inventor: Alan R. Tall, Cresskill, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/560,372

(22) Filed: Apr. 28, 2000

(51) Int. Cl.$^7$ .................... G01N 33/53; G01N 33/567; C07H 21/04; C12N 15/00; C12N 15/09
(52) U.S. Cl. .................... 435/7.2; 536/24.1; 435/320.1; 435/325
(58) Field of Search .................... 536/24.1, 23.1, 536/23.5; 435/320.1, 325, 7.2, 455; 514/44

(56) References Cited

PUBLICATIONS

IM Verma et al., Nature, "Gene therapy–promises,problems and prospects," Sep. 1997, vol. 389, pp. 239–242.*
WF Anderson, Nature, "Human gene therapy," Apr. 1998, vol. 392, pp. 25–30.*
Huang et al. Depression of human embryonic z–globin promoter by a locus–control region sequence. PNAS. 1998. vol. 95. pp. 14669–14674.*
Brousseau, M.E. et al., "Novel Mutations in the Gene Encoding ATP Binding Cassette 1 In Four Tangier Disease Kindreds", *J. Lipid Res.,* 41(3): 433–441, Mar. 2000; (Exhibit 1).
Brown, M.S. et al., "The SREBP Pathway: Regulation of Cholesterol Metabolism by Proteolysis of a Membrane–bound Transcription Factor", *Cell,* 89(3):331–340. May 1997; (Exhibit 2).
Bodzioch, M. et al., "The Gene Encoding ATP–Binding Cassette Transporter 1 is Mutated in Tangier Disease" *Nat. Gen.,*22(4):347–351, Aug. 1999; (Exhibit 3).
Bruce, C. et al., "Plasma Lipid Transfer Proteins High density Lipoprotein, and Reverse Cholesterol Transport", *Annual Rev. Nutr.,* 18:297–330, 1998; (Exhibit 4).
Castelli, W. P. et al., "Incidence of Coronary Heart Disease and Lipoprotein Cholesterol Levels", *JAMA,* 256(20):2835–2838, Nov. 1986; (Exhibit 5).
Christenson, L. K. et al., "Oxysterol Regulation of Steroidogenic Acute Regulatory Protein Gene Expression", *J. Biol. Chem.,* 273(46): 30729–30735, Nov. 1998; (Exhibit 6).
Croop, J. M., "Evolutionary Realtionships among ABC Transporters", *Methods Enzymol,* 292: 101–116, 1998: (Exhibit 7).
Feltkamp, D. et al., "Identification of a Novel DNA binding site for Nuclear Orphan Receptor OR1", J. Biol. Chem., 274(15): 10421–10429, Apr. 1999; (Exhibit 8).
Hamon, Y. et al., "Interleukin–1beta Secretion is Imparied by Inhibitors of the ATP Binding Cassette Transporter, ABC1", *Blood,* 90(8): 2911–2915, Oct. 1997; (Exhibit 9).

Hultén, L. M. et al., "Oxysterols presents in Atherosclerotic Tissue Decrease the Lipoprotein Lipase Messenger RNA in Human Monocyte–Derived Macrophages", J.Clin. Invest., 97(2): 461–468, Jan. 1996; (Exhibit 10).
Janowski, B.A. et al., "An Oxysterol Signaling Pathway Mediated by the Nuclear Receptor LXR Alpha" Nature, 383: 728–731, Oct. 1996; (Exhibit 11).
Klucken, J. et al., "ABCG1 (ABC8), The Human Homolog of the Drosophilia White Gene is a Regulator of Macrophage Cholesterol and Phospholipid Transport", *Proc. Natl. Acad. Sci.,* 97(2): 817–822, Jan. 2000; (Exhibit 12).
Kronqvist, R. et al., "The Effect of Interleukin 1 Beta on the Biosynthesis of Cholesterol, Phosphatidylcholine, and Sphingomyelin in Fibroblasts, and on Their Efflux from Cells to Lipid–Free Apolipoprotein A–I", *Eur. J. Biochem.,* 262(3): 939–946; (Exhibit 13).
Lala, D.S. et al., "Activation of the Orphan Nuclear Receptor Steroidogenic Factor 1 by Oxysterols", *Proc. Natl. Acad. Sci.,* 94(10): 4895–4900, May 1997; (Exhibit 14).
Langman, T. et al., "Molecular Cloning of the Human ATP–Binding Cassette Transporter 1 (hABC1): Evidence for Sterol–Dependent Regulation in Macrophages", *Biochem.Biophys. Res. Commun.,* 257(1):29–33, Apr. 1999; (Exhibit 15).
Lawn, R. M. et al., The Tangier Disease Gene Product ABC1 Controls the Cellular Apolopoprotein–Mediated Lipid Removal Pathway, *J. Clin. Invest.,* 104(8): 25–31, Oct. 1999; (Exhibit 16).
Lehmann, J. M. e al., "Activation of the Nuclear Receptor LXR by Oxytsterols Defines A New Hormone Response Pathway", *J. Biol. Chem.,* 272(6):3137–3140, Feb. 1997; (Exhibit 17).
Luciani, M.F. et al., "Cloning of Two Novel ABC Transporter Mapping on Human Chromosome 9", *Genomics,* 21:(1) 150–159, May 1994; (Exhibit 18).
Luo, Y. et al., "Sterol Upregulation of Human CETP Expression In Vitro and in Transgenic Mice by an LXR Element", *J. Clin. Invest.,* 105: 513–520, Feb. 2000; (Exhibit 19).
Marcil, M. et al., "Cellular Cholesterol Transport and Efflux in Fibroblasts are Abnormal in Subjects with Familiar HDL Deficiency", *Arterioscler. Thromb. Vase. Biol.,* 19(1): 159–169 Jan. 1999; (Exhibit 20).

(List continued on next page.)

Primary Examiner—Peter Paras, Jr.
(74) Attorney, Agent, or Firm—John P. White; Cooper & Dunham LLP

(57) ABSTRACT

Disclosed is the sequence of the human ABC1 promoter, a method for expressing foreign DNA in host cells using the human ABC1 promoter, including a method of determining whether a chemical not previously known to be a modulator of the human ABC1 gene transcriptionally modulates the expression of the human ABC1 gene. Also disclosed is a sterol-responsive region of the human ABC1 promoter, along with a showing that it is activated by hydroxysterols and 9-cis-retinoic acid, implicating a mechanism of activation involving LXR/RXR heterodimers.

24 Claims, 10 Drawing Sheets

OTHER PUBLICATIONS

Marcil, M. et al., "Mutations in the ABC1 Gene in Familial HDL Deficiency with Defective Cholesterol Efflux", *Lancet*, 354(9187): 1341–1346 Oct. 1999; (Exhibit 21).

Ohlsson, B. J. et al., "Oxidized Low Density Lipoprotein Inhibits Lipopolysaccharide–Induced Binding of Nuclear Factor–KappaB to DNA and the Subsequent Expression of Tumor Necrosis Factor–alpha and Interleukin–1 beta in Macrophages", *J. Clin. Invest.*, 98(1): 78–89, Jul. 1996; (Exhibit 22).

Orso, E., et al., "Transport of Lipids from Golgi To Plasma Membrane is Defective in Tangier's Disease Patients and ABC1–deficient Mice", *Natural Genetics*, 24(2):192–196, Feb. 2000; (Exhibit 23).

Panousis, C.G. et al., "Regulation of Cholesterol Distribution in Macrophage Derived Foam Cells by Interferon–gamma", *J. Lipid Res.*, 41(1): 75–83, Jan. 2000 (Exhibit 24).

Peet, D.J. et al., "Cholesterol and Bile Acid Metabolism Are Impaired in Mice Lacking the Nuclear Oxysterol Receptor LXR Alpha", *Cell*, 93(5): 693–704, May 1998; (Exhibit 25).

Remaley, A. T. et al., "Decreased Reverse Cholesterol Transport From Tangier Disease Fibroblasts. Acceptor Specificity and Effect of Brefeldin On Lipid Efflux", *Arterioscler Thromb. Vasc. Biol.*, 17(9):1813–1821, Sep. 1997; (Exhibit 26).

Remaley, A. T. et al., "Human ATP–Binding Cassette Transporter 1 (ABC):Genomic Organization and Identification of the Genetic Defect in the Original Tangier Disease Kindred" *Proc. Natl. Acad. Sci.*, 96(22): 12685–13690, Oct. 1996; (Exhibit 27).

Rothblat, G. H. et al., "Cell Cholesterol Efflux: Integration of Old and New Observations Provides New Insights", *J. Lipid Res.*, 40(5): 781–796, May 1999; (Exhibit 28).

Rust, S. et al., "Assignment of Tangier Disease to Chromosome 9q31 By a Graphical Linkage Exclusion Strategy", *Natural Genetics*, 20(1): 96–98, Sep. 1998; (Exhibit 29).

Rye, K. A. et al., "Evidence that Cholesterol Ester Transfer Protein–Mediated Reductions in reconstituted High density Lipoprotein size Involve Particle Fusion", *J. Biol. Chem.*, 272(7): 3953–3960, Feb. 1997; (Exhibit 30).

Seol, W. et al., "Isolation of Proteins that Interact Specifically With the Retinoid X Receptor: Two Novel Orphan Receptors", *Mol. Endocrinol*, 9(1): 72–85, Jan. 1995; (Exhibit 31).

Song C. et al., "Ubiquitous Receptor: A Receptor that Modulates Gene Activation By Retinoic Acid and Thyroid Hormone Receptors", *Proc. Natl. Acad Sci.*, 91(23): 10809–10813, Nov. 1994; (Exhibit 32).

Teboul, M. et al., "OR–1, A Member of the Nuclear Receptor Superfamily That Interacts With the 9–cis–retinoic Acid Receptor", *Proc. Natl. Acad Sci.*, 92(6): 2096–2100, Mar. 1995; (Exhibit 33).

Shipley, J. M., "Metalloelastase is Required for Macrophage–Medicated Proteolysis and Matrix Invasion in Mice", *Proc. Natl. Acad Sci.*, 93(9): 3942–3946, Apr. 1996; (Exhibit 34) and.

Willy, P. J., "LXR, A Nuclear Receptor that Defines A Distinct Retinoid Response Pathway", *Genes Dev.*, 9(9): 1033–1045, May 1995; (Exhibit 35).

Schmitz et al., "Structure, function and regulation of the ABC1 gene product", Current Opinion in Lipidology, 2002, vol. 12, 129–140 (Exhibit 1).

PCT International Search Report dated Aug. 14, 2001 issued in the corresponding PCT International Application No. PCT/US01/13654 (Exhibit 2).

* cited by examiner

FIGURE 2A
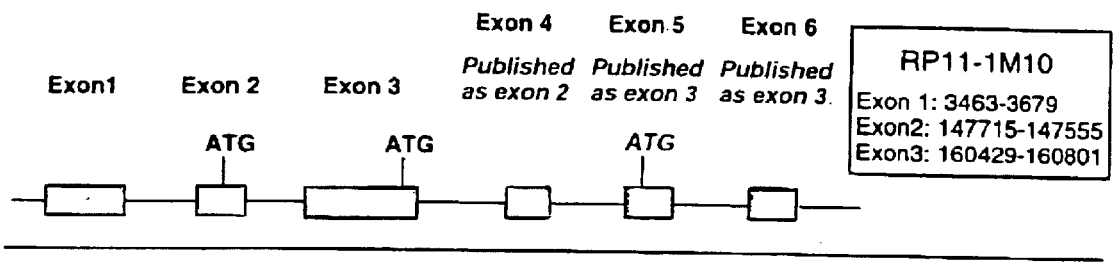
FIGURE 2B
THP-1
A
HepG2
B
C
D
FIGURE 2C
```
              1                      22                                            61
A, B   MACWPQLRVLLWKNLTFRRRQTCQLLLEVAWPLFIFLILISVRLSYPPYEQHECHFPNKAM
C, D                        MCQLLLEVAWPLFIFLILISVRLSYPPYEQHECHFPNKAM
```

FIG. 3 acctgagttttggccagaataaggtgacatttagtttgttggcttgatggatgacttaaatatttagacatatggtg
<u>　　　　　　　　　　　　　　　　　　　　　　　　　　　　　　　　　　atgacttaaatatttaga</u>
　　　　　　　　　　　　　　　　　　　　　　　　　　　　　　　　　　CREBP1CJUN tgtaggcctgcattcctactcttgccttttttttgcccctccagtgttttgggtagttttgctcccctacagccaaagg
　-928bp caaacagataagttggaggtctggagtggctacataattttacacgactgcaattctctggctgcacttcacaa atgtatacaaactaaatacaagtcctgtgttttatcacagggaggctgatcaatataatgaaattaaaagggg
　　　　　　　　　　　　　　　　　　　　　　　　　　　　　　　　　　　　<u>　　　CEBPB　</u> gctggtccatattgttctgtgttttgtttgtttgtttctttttttgttttgtggcctccttcctctcaatttatgaagagaagc
　　　　　　　　　　<u>　HNF3B　</u><u>　IRF1　</u> agtaagatgttcctctcgggtcctctgagggacctggggagctcaggctgggaatctccaaggcagtaggtc
　　　　　　　　　　　　　　　　　　　　　　　　　　　　<u>　　NF-KB　　</u> gcctatcaaaaatcaaagtccaggtttgtggggggaaaacaaaagcagcccattacccagaggactgtcc gccttcccctcaccccagcctaggcctttgaaaggaaacaaaagacaagacaaaatgattggcgtcctgag ggagattcagcctagagctctctctccccaatccctccctccggctgaggaaactaacaaaggaaaaaaaa
　　　　　　　　　　▲ Sac1 attgcggaaagcaggatttagaggaagcaaattccactggtgcccttggctgccgggaacgtggactagag
　　　　　　　　　　　<u>　　　　　　</u>
　　　　　　　　　　　Stat1 agtctgcggcgcagccccgagcccagcgcttcccgcgcgtcttaggccggcgggcccgggcggggaag gggacgcagaccgcggaccctaagacacctgctgtaccctccaccccaccccacccacctcccccaa ctccctagatgtgtcgtgggcggctgaacgtcgcccgtttaaggggcgggccccggctccacgtgctttctgct
　　　　　　　　　　　　　　　　　　　　　　　　　　　　　　　　　　　<u>　MYCMAX　</u> gagtgactgaactacataaacagaggccgggaacggggcggggagggagagcacaggctttgac
<u>　　　　　</u>　　　　　　　　　　　　　　<u>　　　　　　　　　</u>
　AP1　　　　　　　　　　　　　　　　　　SP1 cgatagtaacctctgcgctcggtgcagccgaatc<u>TATAA</u>aaggaactagtcccggcaaaaacccgtaa ttgcgagcgagagtgagtggggccgggacccgcagagccgagccgaccttctctcccgggctg
　　　　　　　　　　　　　　　　　　　　　　　　　　　　　　　　+101 cggcagggcagggcggggagctccgcgcaccaacagagc

ABC1-T: 61 MPSAGT--- (Genebank Accession: X75926; the methionine 61 here was originally designated as the start methionine. This version of cDNA is inactive in stimulating cholesterol efflux.)

ABC1:  1  MACWPQLRLLLWKNLTFRRRQTCQLLLEVA
       31 WPLFIFLILISVRLSWPPYEQHECHFPNKA
       61 MPSAGT---

HUMAN ABC1 PROMOTER AND ASSAYS BASED THEREON

This invention has been made with government support under National Institutes of Health Grant No. HL-54591. Accordingly, the U.S. Government may have certain rights in the invention.

Throughout this application, various publications may be referenced by Arabic numerals in brackets. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

FIELD OF INVENTION

This invention discloses a sterol-responsive region of the human ABC1 promoter, and shows that it is activated by hydroxysterols and 9-cis-retinoic acid, implicating a mechanism of activation involving LXR/RXR heterodimers. Also disclosed is the functionally active form of the ABC1 cDNA.

BACKGROUND OF THE INVENTION

Plasma HDL-C levels are inversely related to the incidence of coronary artery disease (1). Two genetic diseases illustrate this phenomenon: the rare Tangier Disease and the more common familial HDL deficiency. Tangier disease is characterized by an extremely low concentration of circulating HDL and the accumulation of cholesteryl esters in tonsils, liver, spleen and intestinal mucosa, mostly in macrophage foam cells (2). Patients with familial HDL deficiency exhibit a low concentration of HDL particles and an increased risk of coronary artery disease (3). A common explanation for the cardioprotective effect of HDL is the major role they play in reverse cholesterol transport (4). It is commonly accepted that the efflux of cholesterol from cells is due to two different pathways: the first is passive and promotes efflux from the cell membrane to HDL, and the second is energy-dependent and apolipoprotein-mediated (5). The latter was characterized in fibroblasts and macrophages, and involves lipid-poor or lipid-free apolipoproteins such as apoA-I, apoA-II and apo-E (5). This active pathway has been reported to be defective in both Tangier disease and familial HDL deficiency (6–7). It was recently shown that ABC1 is a key gene in this process (8) and that mutations in this gene are the major cause of Tangier disease and familial HDL deficiency (3, 9–14).

ABC1 (ABCA1) belongs to the large ATP-Binding Cassette transporter family. These transmembrane proteins transport many substrates across membranes thanks to a channel-like topology (15–16). The human ABC1 gene was assigned to chromosome 9q31, spanning a minimum of 70 kb and containing at least 49 exons (11, 13, 17). While its expression is ubiquitous, the highest levels of human or murine mRNAs were found in placenta, liver, lung, adrenal glands and fetal tissues (18, 19). The predicted human protein contains 2201 amino acids (220 kDa) (18).

The expression of hABC1 is induced during differentiation of human monocytes to macrophages and as a result of cholesterol loading. In human macrophages, both the protein and the mRNA are upregulated in the presence of acetylated LDL (acLDL), and downregulated by cholesterol unloading via HDL3 (18). While the cholesterol-mediated downregulation of genes involved in cholesterol uptake or biosynthesis is well understood (20), mechanisms of sterol-mediated upregulation of gene expression are more poorly understood. Two families of nuclear receptors are known to be activated by oxysterols and to mediate a positive response by binding to specific DNA elements: Liver-X-Receptor (LXR) and Steroidogenic Factor 1 (SF1) (21), (22), (23), (24). SF1 acts as a monomer and has been implicated, for example, in the regulation of steroidogenic acute regulatory protein gene expression (StAR) (23). Recently, two different genes involved in reverse cholesterol transport pathways, cyp7a (21) and CETP (22), have been shown to be upregulated by the heterodimer LXR-RXR (Liver-X-Receptor and Retinoid-X-Receptor). This suggests the hypothesis that LXRs might coordinate different steps of these pathways (22). LXRα (NR1H3) and LXRβ (NR1H2) heterodimerize with their partner RXR to upregulate genes through binding sites composed of direct repeats (DR) spaced by 4 (LXRα and LXRβ) or 1 nucleotide (LXRβ) (25–27). The dimer can be activated by both the ligands of RXR (retinoids) and LXR (oxysterols), separately or together (26, 28, 29).

However, none of the cited references disclose the sequence of the hABC1 promoter, nor do they define its function or activation by transcription factors or small organic molecules.

SUMMARY OF THE INVENTION

This disclosure provides an isolated human ABC1 promoter capable of directing transcription of a heterologous coding sequence positioned downstream therefrom, wherein the promoter is:
  (a) a promoter comprising the nucleotide sequence shown in SEQ ID NO: 1;
  (b) a promoter comprising a nucleotide sequence functionally equivalent to the nucleotide sequence shown in SEQ ID NO: 1; or
  (c) a promoter comprising a nucleotide sequence that hybridizes to a sequence complementary to the promoter of (a) or (b) in a Southern hybridization reaction performed under stringent conditions.

This disclosure also provides a recombinant expression construct effective in directing the transcription of a selected coding sequence which comprises:
  (a) a human ABC1 promoter nucleotide sequence according to claim 1; and
  (b) a coding sequence operably linked to the promoter, whereby the coding sequence can be transcribed and translated in a host cell, and the promoter is heterologous to the coding sequence.

This disclosure also provides a method for expressing foreign DNA in a host cell which comprises introducing into the host cell a gene transfer vector comprising the discussed ABC1 promoter operably linked to a foreign DNA encoding a desired polypeptide or RNA, wherein said foreign DNA is expressed.

The disclosure also provides a method of determining whether a chemical not previously known to be a modulator of the human ABC1 gene transcriptionally modulates the expression of the human ABC1 gene which comprises:
  (a) contacting a sample which contains a predefined number of identical eucaryotic cells with a predetermined concentration of the chemical to be tested, each cell comprising a DNA construct consisting essentially of in 5' to 3' order,
    (i) a modulatable transcriptional regulatory sequence of the ABC1 gene,
    (ii) the ABC1 promoter of claim 1, and
    (iii) a reporter gene which expresses a polypeptide that produces a detectable signal, coupled to, and under the control of, the ABC1 promoter, under conditions wherein the chemical if capable of acting as a transcriptional modulator of the ABC1 gene, causes a detectable signal to be produced by the polypeptide expressed by the reporter gene;

(b) quantitatively determining the amount of the signal produced in (a); and (c) comparing the amount of signal determined in (b) with the amount of signal produced and detected in the absence of any chemical being tested or with the amount of signal produced and detected upon contacting the sample in (a) with other chemicals, thereby identifying the test chemical as a chemical which causes a change in the amount of detectable signal produced by the polypeptide expressed by the reporter gene, and determining whether the test chemical specifically transcriptionally modulates expression of the human ABC1 gene.

This disclosure also provides a method of treating atherosclerosis in a subject which comprises administering to the subject a therapeutically effective amount of a chemical selected by the method discussed above to modulate expression of the human ABC1 gene.

This disclosure also provides a transgenic non-human mammal whose germ or somatic cells contain the promoter described herein introduced into the mammal, or an ancestor thereof, at an embryonic stage. The mammal may be a mouse.

This disclosure also provides a compound which modulates expression of the human ABC1 gene, which has been identified by the method discussed above.

This disclosure also provides an isolated human ABC1 gene comprising six exons and the promoter described.

Thus, disclosed is the sequence of the hABC1 promoter and its 5' untranslated region, with 3 new exons, differentially expressed and carrying two alternative start codons. This promoter is active in macrophages. Also, the full length cDNA, incorporating the 3 new exons plus the published cDNA sequence, is active in promoting efflux of cholesterol from cells, while the published cDNA sequence alone is not. Also disclosed is that RXRα and LXRα or LXRβ are able to activate in vitro this promoter and the response is increased by oxysterols and/or 9-cis-retinoic acid (9CRA).

DESCRIPTION OF THE FIGURES

FIGS. 2A–2C show the analysis of the hABC1 5' sequence. FIG. 2A shows the gene organization. The hABC1 promoter was cloned from the human library RPCI-11, and the structure of its 5' end was determined. FIG. 2B shows the results of 5' RACE PCR. A 5' RACE PCR was performed on cholesterol-loaded THP-1 macrophages. These cells express exon 1 and 2 (transcript A). A 5'RACE PCR was also conducted on HepG2 cells which express a truncated version of exon 2 and also exon 3 (transcripts B, C, D). Two ATG are present in exon 2 and 3. FIG. 2C shows the NH2 terminal sequence. A comparison of the deduced NH2 terminal sequence of hABC1 with the nucleotide database (tBlastn) revealed similarities with two members of the ABC1 family: ABCR and ABC3. A,B=SEQ ID NO: 2; C,D=SEQ ID NO: 3; amino acids 6–61 of hABC1=SEQ ID NO: 4; amino acids 6–61 of hABCR=SEQ ID NO: 6; amino acids 1∝44 of hABC1=SEQ ID NO: 5; and amino acids 1–44 of hABC3=SEQ ID NO: 7.

FIG. 3 shows the hABC1 promoter sequence (SEQ ID NO: 1). This sequence is identical to the working draft sequence of the genomic clone RPM11-1M10 (position 2335 bp to 3463 bp, genebank accession number AC012230) except for the italicized 5' end which is new. The fragment used in transfections covers −928 bp to +101 bp. An arrow indicated at −469 bp is the Sac1 site that was used to generate a deleted promoter fragment. An analysis of the sequence (Matinspector) revealed numerous putative transcription binding sites (underlined, dashed lines indicate a site on the complementary strand). The bold type represents the 5' end of exon 1.

In FIG. 5A a fragment of the hABC1 promoter (−828 bp to +101 bp) was linked to Firefly luciferase reporter gene. The resulting plasmid was cotransfected with a control reporter plasmid (Renilla luciferase) in the mouse macrophage-like RAW 264.7 cells. Four independent transfections experiments (each in triplicates) were performed. The results are expressed as a ratio between the Firefly and Renilla luciferase activities. Cells were treated with vehicle or 22(R)-Hch (10 µM), 9CRA (10 µM) and 22(R)-Hch (10 µM)+9CRA (10 µM), 24 hours in FBS medium complemented with 10% LPDS. FIG. 5B shows deletional analysis of hABC1 promoter. Two independent experiments in triplicate were performed according to the protocol described in (a), using a shorter promoter: −456 pb +101 pb. FIG. 5C shows activation of hABC1 promoter by various oxysterols and/or 9CRA. The same experiments as (a) were performed using 22(R)-Hch (10 µM), 25-Hch (10 µM), 7K-Ch (10 µM) and 9CRA (10 µM). Three to four independent experiments in duplicate or triplicate were performed. Mann Whitney tests were mean to analyze the difference between "Ethanol" and "Treatment". In these Figures, ***=P<0.001,*=P<0.05.

In FIG. 6A 293 cells were transfected with the hABC1 promoter (−469 bp +101 bp) or in FIG. 6B a construct containing 3 copies of the LXR responsive element of the CETP promoter (22). These constructs were cotransfected with the Renilla luciferase reporter gene and hLXRα, mLXRβ, hRXRα. The cells were treated 24 h with vehicle alone or 22(R)-Hch (10 µM) and/or 9CRA (10 µM) in FBS medium+10% LPDS. The results represent two independent experiments in duplicates for the transfections using the hABC1 promoter and one to two experiments in duplicate for the transfections using the hCETP promoter.

FIG. 8A shows results of a study using Genebank Accession X75926, where the methionine 61 was originally designated as the start methionine. This version of cDNA is inactive in stimulating cholesterol efflux. FIG. 8B shows results of a study using the full length version, including exons 1–3, encoding an additional 60 amino acids, which is active in promoting cholesterol efflux to apoAl.

DETAILED DESCRIPTION OF THE INVENTION

Figure 1:
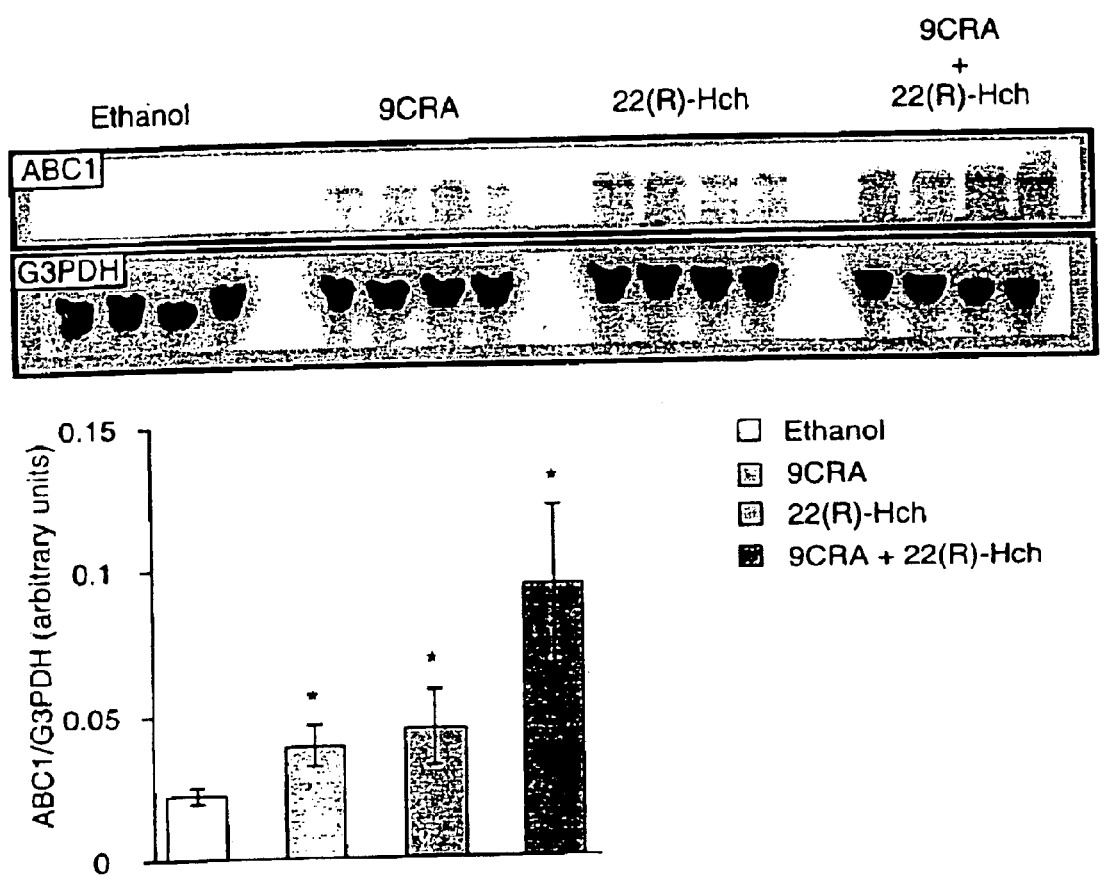
FIG. 1 shows the expression of hABC1 in THP1 macrophages. THP-1 cells were exposed for 72 h to phorbol 12-myristate 13-acetate to induce their differentiation in macrophages. On day 4, cells were treated for 24 h with vehicle (ethanol), 22(R)-Hch (10 mM) and/or 9CRA (10 mM) (n=4 per treatment). A Northern blot was performed with 40 µg of total RNA from each sample. The membrane was hybridized with hABC1 probe and mG3PDH as an internal standard. The Mann Whitney test was used to analyse the difference between "ethanol' and "treatment", *p<0.05.

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, Molecular Cloning: A Laboratory Manual, -Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I–IV (D. M. Weir and C. C. Blackwell eds., 1986, Blackwell Scientific Publications).

This disclosure provides an isolated human ABC1 promoter capable of directing transcription of a heterologous coding sequence positioned downstream therefrom, wherein the promoter is:
  (a) a promoter comprising the nucleotide sequence shown in SEQ ID NO: 1;
  (b) a promoter comprising a nucleotide sequence functionally equivalent to the nucleotide sequence shown in SEQ ID NO: 1; or
  (c) a promoter comprising a nucleotide sequence that hybridizes to a sequence complementary to the promoter of (a) or (b) in a Southern hybridization reaction performed under stringent conditions.

The promoter may be a nucleotide sequence that is at least 87% homologous to SEQ ID NO: 1, preferebly 90% homologous to SEQ ID NO: 1, most preferably at least 95% homologous to SEQ ID NO: 1.

This disclosure also provides a recombinant expression construct effective in directing the transcription of a selected coding sequence which comprises:

(a) a human ABC1 promoter nucleotide sequence according to claim 1; and
  (b) a coding sequence operably linked to the promoter, whereby the coding sequence can be transcribed and translated in a host cell, and the promoter is heterologous to the coding sequence.

The recombinant expression construct may further have a coding sequence that encodes a transporter polypeptide. The transporter polypeptide may be ABCA1 transmembrane transporter protein.

The recombinant expression construct may further comprise a nucleic acid segment encoding a transactivator protein capable of upregulating the ABC1 promoter. The transactivator protein may be the Liver-X-Receptor, the Retinoid-X-Receptor, or a heterodimer of the Liver-X-Receptor and the Retinoid-X-Receptor.

This disclosure also provides a host cell which comprises the recombinant expression construct discussed above. The host cell may be stably transformed with the recombinant expression construct.

The host cell may be a macrophage, an immortalized cell, a RAW cell, an African green monkey CV-1 cell, or a human 293 cell.

This disclosure also provides a method for expressing foreign DNA in a host cell which comprises introducing into the host cell a gene transfer vector comprising the discussed ABC1 promoter operably linked to a foreign DNA encoding a desired polypeptide or RNA, wherein said foreign DNA is expressed.

The promoter nucleotide sequence may be a nucleotide sequence functionally equivalent to the ABC1 promoter sequence represented in SEQ ID NO: 1.

In the method, the gene transfer vector may encode and expresse a reporter molecule. The reporter molecule may be selected from the group consisting of beta-galactosidase, beta-glucuronidase, luciferase, chloramphenicol acetyltransferase, neomycin phosphotransferase, and guanine xanthine phosphoribosyltransferase.

The vector may be introduced into the cell adenovirus infection, liposome-mediated transfer, topical application to the cell, or microinjection.

The method may further comprise introducing into the cell a gene transfer vector comprising a nucleic acid segment encoding a transactivator protein capable of upregulating the ABC1 promoter. The transactivator protein may be the Liver-X-Receptor, the Retinoid-X-Receptor, or a heterodimer of the Liver-X-Receptor and the Retinoid-X-Receptor.

The method may also comprise contacting the cell with a transactivator protein capable of upregulating the ABC1 promoter. The transactivator protein may be the Liver-X-Receptor, the Retinoid-X-Receptor, or a heterodimer of the Liver-X-Receptor and the Retinoid-X-Receptor.

The method may also comprise contacting the cell with an agonist of the Liver-X-Receptor, of the Retinoid-X-Receptor, or of a heterodimer of the Liver-X-Receptor and the Retinoid-X-Receptor.

The disclosure also provides a method of determining whether a chemical not previously known to be a modulator of the human ABC1 gene transcriptionally modulates the expression of the human ABC1 gene which comprises:
  (a) contacting a sample which contains a predefined number of identical eukaryotic cells with a predetermined concentration of the chemical to be tested, each cell comprising a DNA construct consisting essentially of in 5' to 3' order,
    (i) a modulatable transcriptional regulatory sequence of the ABC1 gene, (ii) the ABC1 promoter of claim 1, and (iii) a reporter gene which expresses a polypeptide that produces a detectable signal, coupled to, and under the control of, the ABC1 promoter, under conditions wherein the chemical if capable of acting as a transcriptional modulator of the ABC1 gene, causes a detectable signal to be produced by the polypeptide expressed by the reporter gene;

(b) quantitatively determining the amount of the signal produced in (a); and (c) comparing the amount of signal determined in (b) with the amount of signal produced and detected in the absence of any chemical being tested or with the amount of signal produced and detected upon contacting the sample in (a) with other chemicals, thereby identifying the test chemical as a chemical which causes a change in the amount of detectable signal produced by the polypeptide expressed by the reporter gene, and determining whether the test chemical specifically transcriptionally modulates expression of the human ABC1 gene.

In the method, each cell may express a transactivator protein capable of upregulating the ABC1 promoter. The transactivator protein may be any of the ones previously mentioned.

The method may also comprise contacting the cells with a transactivator protein capable of upregulating the ABC1 promoter.

In the method, the sample may comprise identical cells in monolayers, or cells in suspension. The identical cells comprise human, animal, or plant cells. The predefined number of identical cells may be from about 1 to about $5 \times 10^5$ cells, preferably from about 1.0 pM to about 20 μM, more preferably from about 10 nM to about 500 μM.

In the method, the contacting may be effected from about 1 hour to about 24 hours. The contacting may be effected with more than one predetermined concentration of the molecule to be tested.

In the method, the modulatable transcriptional regulatory sequence may comprise a cloned genomic regulatory sequence.

The DNA construct may consist of more than one modulatable transcriptional regulatory sequence.

In the method, the reporter gene may be inserted downstream of the ABC1 promoter by homologous recombination. The reporter gene may encode a luciferase, chloramphenicol acetyltransferase, beta-glucuronidase, beta-galactosidase, neomycin phosphotransferase, or guanine xanthine phosphoribosyltransferase. Preferably, the reporter gene is the ABC1 gene.

This disclosure also provides a method of treating atherosclerosis in a subject which comprises administering to the subject a therapeutically effective amount of a chemical selected by the method discussed above to modulate expression of the human ABC1 gene.

This disclosure also provides a method of simultaneously screening a plurality of test chemicals to determine whether the chemicals are capable of transcriptionally modulating the ABC1 gene which comprises simultaneously screening the test chemicals against each of the genes of interest according to the method discussed above.

This disclosure also provides a transgenic non-human mammal whose germ or somatic cells contain the promoter described herein introduced into the mammal, or an ancestor thereof, at an embryonic stage. The mammal may be a mouse.

This disclosure also provides a compound which modulates expression of the human ABC1 gene, which has been identified by the method discussed above.

This disclosure also provides an isolated human ABC1 gene comprising six exons and a promoter, wherein the promoter is selected from the group consisting of:

(a) a promoter comprising the nucleotide sequence shown in SEQ ID NO: 1;

(b) a promoter comprising a nucleotide sequence functionally equivalent to the nucleotide sequence shown in SEQ ID NO: 1; and (c) a promoter comprising a nucleotide sequence that hybridizes to a sequence complementary to the promoter of (a) or (b) in a Southern hybridization reaction performed under stringent conditions.

DEFINITIONS

As used herein "nucleic acid molecule" includes both DNA and RNA and, unless otherwise specified, includes both double-stranded and single-stranded nucleic acids. Also included are hybrids such as DNA-RNA hybrids. Reference to a nucleic acid sequence can also include modified bases as long as the modification does not significantly interfere either with binding of a ligand such as a protein by the nucleic acid or Watson-Crick base pairing.

Two DNA or polypeptide sequences are "substantially homologous" when at least about 80% (preferably at least about 90%, and most preferably at least about 95%) of the nucleotides or amino acids match over a defined length of the molecule. As used herein, "substantially homologous" also refers to sequences showing identity to the specified DNA or polypeptide sequence. DNA sequences that are substantially homologous can be identified in a Southern hybridization, experiment under, for example, stringent conditions, as defined for that particular system. Defining appropriate hybridization conditions is within the skill of the art. See, e.g., Sambrook et al., supra; DNA Cloning, vols I & II, supra; Nucleic Acid Hybridization, supra.

A sequence "functionally equivalent" to an ABC1 promoter sequence is one which functions in the same manner as the ABC1 promoter sequence. Thus, a promoter sequence "functionally equivalent" to the ABC1 promoter described herein is one which is capable of directing transcription of a downstream coding sequence in substantially similiar timeframes of expression and in substantially similar amounts and with substantially similar tissue specificity as the ABC1 promoter.

A DNA "coding sequence" or a "nucleotide sequence encoding" a particular protein, is a DNA sequence which is transcribed and translated into a polypeptide in vivo or in vitro when placed under the control of appropriate regulatory sequences. The boundaries of the coding sequence are determined by a start codon at the 5'-(amino) terminus and a translation stop codon at the 3'-(carboxy) terminus. A coding sequence can include, but is not limited to, procaryotic sequences, cDNA from eucaryotic mRNA, genomic DNA sequences from eucaryotic (e.g., mammalian) sources, viral RNA or DNA, and even synthetic nucleotide sequences. A transcription termination sequence will usually be located 3' to the coding sequence.

DNA "control sequences" refers collectively to promoter sequences, polyadenylation signals, transcription termination sequences, upstream regulatory domains, enhancers, and the like, untranslated regions, including 5'-UTRs and 3'-UTRs, which collectively provide for the transcription and translation of a coding sequence in a host cell.

"Operably linked" refers to an arrangement of nucleotide sequence elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A control sequence "directs the transcription" of a coding sequence in a cell when RNA polymerase will bind the promoter sequence and transcribe the coding sequence into mRNA, which is then translated into the polypeptide encoded by the coding sequence.

A cell has been "transformed" by exogenous DNA when such exogenous DNA has been introduced inside the cell membrane. Exogenous DNA may or may not be integrated (covalently linked) into chromosomal DNA making up the genome of the cell. In eucaryotic cells, a stably transformed cell is generally one in which the exogenous DNA has become integrated into the chromosome so that it is inherited by daughter cells through chromosome replication, or one which includes stably maintained extrachromosomal plasmids. This stability is demonstrated by the ability of the eucaryotic cell to establish cell lines or clones comprised of a population of daughter cells containing the exogenous DNA.

A "heterologous" region of a DNA construct is an identifiable segment of DNA within or attached to another DNA molecule that is not found in association with the other molecule in nature. For example, a sequence encoding a protein other than ABC1 is considered a heterologous sequence when linked to an ABC1 promoter. Similarly, a sequence encoding an ABC1 gene will be considered heterologous when linked to an ABC1 gene promoter with which it is not normally associated. Another example of a heterologous coding sequence is a construct where the coding sequence itself is not found in nature (e.g., synthetic sequences having codons different from the native gene). Likewise, a chimeric sequence, comprising a heterologous structural gene and a gene encoding an ABC1 or a portion of an ABC1, linked to an ABC1 promoter, whether derived from the same or a different ABC1 gene, will be considered heterologous since such chimeric constructs are not normally found in nature. Allelic variation or naturally occurring mutational events do not give rise to a heterologous region of DNA, as used herein.

The phrase "transcriptionally modulate" infers a notion of directness. Thus, as used herein, "transcriptionally modulate" by a molecule means the effect upon transcription of the gene resulting from either (a) direct binding of the molecule to DNA or RNA, a DNA- or RNA-binding protein, and/or a DNA- or RNA-binding protein complex, or (b) direct binding of the molecule to a protein which directly chemically modifies a DNA- or RNA-binding protein or protein complex.

The phrase "specifically transcriptionally modulate expression" as used herein means modulating the expression of the ABC1 gene without modulating the expression of other genes in the cell in a way which would cause an adverse effect on (a) an organism containing the cell in the case where the cell is within the organism or (b) the growth or the culturing of the cell, in the case where the cell is being grown or cultured to make a product where the amount of product produced is associated with expression of a gene-of-interest.

Vectors

Especially preferred are virus based vectors. In the case of eukaryotic cells, retrovirus or adenovirus based vectors are preferred. Such vectors contain all or a part of a viral genome, such as long term repeats ("LTRs"), promoters (e.g., CMV promoters, SV40 promoter, RSV promoter), enhancers, and so forth. When the host cell is a prokaryote, bacterial viruses, or phages, are preferred. Exemplary of such vectors are vectors based upon, e.g., lambda phage. In any case, the vector may comprise elements of more than one virus.

The resulting vectors are transfected or transformed into a host cell, which may be eukaryotic or prokaryotic.

The gene transfer vector of the present invention may additionally comprise a gene encoding a marker or reporter molecule to more easily trace expression of the vector.

This invention will be better understood from the Experimental Details which follow. However, one skilled in the art will readily appreciate that the specific methods and results discussed are merely illustrative of the invention as described more fully in the claims which follow thereafter.

Experimental Details

Tangier Disease, a condition characterized by low HDL and cholesterol accumulation in macrophages, is caused by mutations in ABC1. Consistent with its role in mediating cellular cholesterol efflux, ABC1 is upregulated by cholesterol loading of macrophages. The disclosed study characterized the molecular mechanisms responsible for up-regulation of ABC1 by sterols. In cultured macrophages, ABC1 mRNA was induced in an additive fashion by 22(R)-OH cholesterol+9-cis-retinoic acid (9CRA), suggesting involvement of nuclear hormone receptors of the LXR/RXR family. The 5' end of the human ABC1 transcript was cloned from cholesterol-loaded THP1 macrophages, and 3 new exons and an upstream start codon were found and compared to the published human cDNA sequence. Only a full length cDNA containing these 3 new exons was active in promoting cholesterol efflux when transfected into cells. When transfected into RAW macrophages, the upstream promoter (−469 bp) was induced 7 fold by 22(R)-OH cholesterol, 8 fold by 9CRA and 37 fold by 9CRA +22(R)-OH cholesterol. Furthermore, promoter activity was increased in a sterol-responsive fashion, when co-transfected with LXRα/RXR or LXRβ/RXR in CV1 or HEK293 cells. Also disclosed is a sterol-responsive region of the human ABC1 promoter, along with experiments showing that it is activated by hydroxysterols and 9CRA, suggesting a mechanism involving LXR/RXR heterodimers.

The following abreviations are used throughout this disclosure: 9CRA=9-cis retinoic acid; 22(R)-HCH=22(R)-hydroxycholesterol; 25-HCh=25-hydroxycholesterol; 7-KCh=7-ketocholesterol; DMEM=Dulbecco's modified Eagle's medium; FBS=fetal bovine serum; LPSD=lipoprotein deficient serum; G(3)PDH=Glycerol-3-phosphate dehydrogenase; LXR=liver X receptor; RXR=retinoid X receptor; SF1=steroidogenic factor 1; HNF=hepatocyte nuclear factor; NF-κB=nuclear factor kappa B; CEBP=CAAT-enhancer-binding protein; Ap-1 activator binding protein-1.

Material and Methods

5'RACE PCR

5'RACE PCR were performed with the SMART RACE cDNA kit (Clonetech, Palo Alto, Calif., USA). We used 1 mg poly-$A^+$ mRNA from HEPG2 cells and THP-1 cells, differentiated into macrophage with phorbol 12-myristate 13-acetate, and exposed to acetylated LDL (25 mg/ml) for 48 hours. After the reverse transcription (M-MLV Reverse Transcriptase, Life Technologies, Grand Island, N.Y., USA), a first PCR (hot start, 94C 30", 65C 30", 72C 3', 25 cycles then 72C 10') was performed using this reverse primer: 5'-CCCCCTCCCTCGGGATGCCCGCAGACAA-3' (SEQ ID NO: 8).

A second PCR (hot start, 94C 30", 55 C 30", 72 C 3', 25 cycles then 72C 10') was done on 2.5 ml of the 50 times diluted first PCR sample with the nested primer: 5'-GCCTCCGAGCATCTGAGAACAGGC (SEQ ID NO: 9). The forward primers are provided by Clonetech kit. The different bands obtained by PCR were cloned in TOPOTA cloning vector (Invitrogen, Carlsbad, Calif., USA) and sequenced.

Cloning of hABC1 Promoter and Intron 1 and 2

The screening of the human RPC.11 BAC clones library was performed (Research Genetics, INC, huntsville, Ala., USA) with a 68mer oligo probe corresponding to the base 11 to 79 of the published hABC1 sequence (genebank accession number NM_005502). 5 BAC clones gave a strong hybridization signal. 2 of them were positive by PCR for exon 1 (BAC553F19, primers 5'-TAATTGCGAGCGAGAGTGAGTGGG-3' (SEQ ID NO: 10) (forward), 5'-CCTACCCCTTGACAAGCCTTCC-3' (SEQ ID NO: 11) (reverse)) and exon 3 (BAC 522C12, primers 5'-GGTTGTGTGTATTTAGCACAGCAGGTTGG) (SEQ ID NO: 12) (forward), 5'-TGCTTCCTATCGTGCTTTATCTGGTTCAC-3' (SEQ ID NO: 13) (reverse)). After digestion by Pst1, a southern blot was performed using the $^{32}$P radiolabelled probes generated by PCR with the previously cited exons. Positive bands were cloned in pBluescript KS (+) (Stratagene, La Jolla, Calif., USA). A colony hybridization (probes used for southern blot) (30) allowed us to isolate positive clones for the hABC1 promotor (5 kb) and intron 2. Serendipitously, the sequencing results (performed on both strands) showed that we cloned also intron 2 from BAC 522C12. The sequences of these introns are contained in the sequence of human genomic clone RP11-1M10 (Genebank accession number AC012230) wich contains exon 1 (3463 bp to 3679 bp), exon 2 (147555 bp to 147715 bp) and exon 3 (160429 bp to 160801 bp).

Cell Cultures and Transfection Experiments

The cell lines were purchased from ATCC (Rockville, Md., USA). The murine RAW 264.7, African green monkey CV-1, and human 293 or HepG2 cell lines were maintained in Dulbecco's modified Eagle's medium (DMEM) with 10% Fetal Bovine Serum (FBS), 100 U/ml penicillin and 100 mg/ml streptomycin. THP-1 cells were maintained in RPMI-1640 containing L-glutamine, 10% heat inactivated FBS, 100 U/ml penicillin and 100 mg/ml streptomycin supplemented with 0.5 mM B-mercaptoethanol. Confluent cells were differentiated with 0.2 mM phorbol 12-myristate 13-acetate (Sigma Chemical Co., St Louis, Mo., USA) in ethanol during 72 hours. Thioglycollate-elicited peritoneal macrophages were isolated from C57 Bl/6 mice as described (31).

Transfections were performed in 24-wells plates with Lipofectamine reagent (transactivation experiments in CV-1 and 293 cells, FIG. 6–7) or Lipofectamine-Plus reagent (Basal activation experiments in RAW 264.7, FIG. 5) according to the manufacturer's instructions (Life Technologies, Grand Island, N.Y., USA). For basal activation experiments a total of 0.15 mg of reporter DNA and 0.05 mg of PRL-CMV(Renilla) (Promega Corp., Madison, Wis., USA) per well were used. For transactivation studies we used, per well, 0.025 mg of PRL-CMV, 0.2 mg of reporter DNA and 0.1 mg of each receptors (CMX-hRXRα, CMX-hLXRα, CMV-mLXRβ) or 0.2 mg of pcDNA3. The transfected cells were cultured in lipoprotein deficient serum (LPDS) medium in the presence of 4 mg/ml of 22(R)-hydroxycholesterol (22(R)-HCh), 25-hydroxycholesterol (25-HCh) or 7-ketocholesterol (7-KCh), 10 mM 9-cis retinoic acid (9CRA) (Sigma Chemical Co., St Louis, Mo., USA) or ethanol alone for 24 hours. The luciferase activities were measured using Promega Dual Luciferase assay system. Reporter plasmid used to analyse the activity of hABC1 promoter was constructed by subcloning a 1029 bp PCR fragment of hABC1 promoter (−928 bp +101 bp) into pGL3-Luc basic vector (Promega). The sequence of the PCR fragment was verified. A shorter promoter (−469 bp to +101 bp) was generated by digestion of this plasmid with Sac1. Where shown, error bars represent the standard deviation.

Northern Blot Analysis

Cells were cultured and treated according to the paragraph "cell cultures and transfection experiments". Total RNA were isolated with RNAzol B reagent (TEL-TEST, Inc., Friendwood, Tex., USA). Northern blots were performed as described elsewhere (30). A human ABC1 probe corresponding to exon 2 to 8 of the published sequence was synthesized by RT-PCR (5'-AGGTGGCCTGGCCTCTATTTATCTTC-3' (SEQ ID NO: 14) (forward) and 5'-GCCTCCGAGCATCTGAGAACAGGC-3' (SEQ ID NO: 15) (reverse). LXR probes are synthesized from human LXRα and mouse LXRβ sequences (25), (32). mouseG(3)PDH probe was used as an internal standard (RT-PCR synthesized fragment, primers: 5'-ACCACAGTCCATGCCATCAC-3' (SEQ ID NO: 16) (forward), 5'-TCCACCACCCTGTTGCTGTA-3' (SEQ ID NO: 17) (reverse)).

Informatics Analysis

Nucleotide sequences were analysed using "Sequence Tools" (retrieved from internet: <URL:http://www.path.cam.ac.uk/~pd213/tool_multi.html≧) and BLAST from NCBI (retrieved from internet: <URL:http://www.ncbi.nlm.nih.gov/BLAST/≧). The search for transcription binding sites was performed by MatInspector public domain (retrieved from internet: <URL:http://genomatix.gsf.de/cqi-bin/mathinspector/matinspector.pl≧).

RESULTS

Increased ABC1 mRNA in Human Macrophages Treated with Sterols and/or Retinoic Acid.

To investigate the activation of the endogenous ABC1 gene by oxysterols and/or retinoic acid in macrophages, we performed Northern blot analysis of total RNA from human THP-1 macrophages. FIG. 1 shows a significant increase of ABC1 mRNA in cells treated with 22(R)-HCh (2 fold induction, P<0.05) or 9CR (2 fold, P<0.05). An additive effect was obtained with combined treatment (4 fold, P<0.05 when compared with separate treatments).

Characterization of the 5' end of the hABC1.

In order to identify the promoter of the human ABC1 gene, we performed 5' RACE PCR using poly-A'mRNA from cholesterol loaded THP-1 macrophages and HepG2 cells (FIG. 2B). This revealed a single major transcript (A) consisting of a first exon of 217 bp followed by a second exon of 160 bp, 73% identical to mouse exon 1 (genebank accession number X75926). This exon is then followed by the published human exons 2, 3, 4 (genebank accession number NM_005502).

In HepG2 cells 5" RACE PCR revealed 3 different transcripts (FIG. 2B). Transcript B represents a truncated version of exon 2 found in THP-1 cells (only the 29 last bases) followed by the published exon 2, 3, 4. Transcript C contains one exon of 372 bp upstream of the published exon 2, different to the exons found in THP1 cells. Transcript D has the same 5'structure as transcript C but lacks the published exon 3.

A Blast search in the Genebank database (htgs) revealed 100% homology of these exons (1–3, FIG. 2A) with fragments of the human genomic clone RP11-1M10 (working draft sequence, genebank accession number AC012230). A comparison of the sequence from the published exon 2 (genebank accession number NM_005502) and the 5'RACE PCR product and RP11-1M10 revealed a C instead of a T at position +15 and a G instead of a A at position 17.

Conceptual translation of the transcripts, revealed two new start codons, in frame with the previously published ATG located in exon 5 (11) (FIG. 2A, C). In the case of the transcript characteristic of THP1 cells, a new ATG, located in exon 2, resulted in an extra 60 amino-acid peptide. In the case of HepG2 cells, a new start codon, at the 3' end of exon 3 may be functional in transcript C and also transcript D, which lacks the previously published start codon. This results in an extra 39 amino acid peptide for transcript C.

A comparison of the putative N-terminal amino acid sequences of ABC1 (transcripts A, B) with nucleotide databases revealed strong homology to the N-terminal sequence of two members of the ABC1 family (57% identity with ABCR and 45% identity with ABC3 (FIG. 2C). This strongly suggest that this N-terminal sequence of hABC1 is authentic.

Sequence of hABC1 Promoter.

The promoter region upstream of exon 1 was responsive to sterols when transfected into cells (see below), while the 2.3 kb region upstream of transcript B was not responsive (data not shown). Thus, we focused our attention on the former region.

FIG. 3 presents a partial sequence of genomic DNA with a fragment of exon 1, cloned from the human RPCI.11 BAC library. A potential TATA box element is present at −32 bp and an Sp1 site at −101 bp. An analysis of this sequence revealed several potential binding sites for different transcription factors: $C/EBP_B$, NF-κB, GATA1, $HNF3_B$, NF1. There was no obvious consensus element for LXR/RXR (DR1 or DR4). However it is known that these nuclear receptors can bind degenerate elements, as shown for the CETP promoter (22).

hABC1 Promoter is Functional and Sterol Responsive in Macrophages.

Figure 5A:
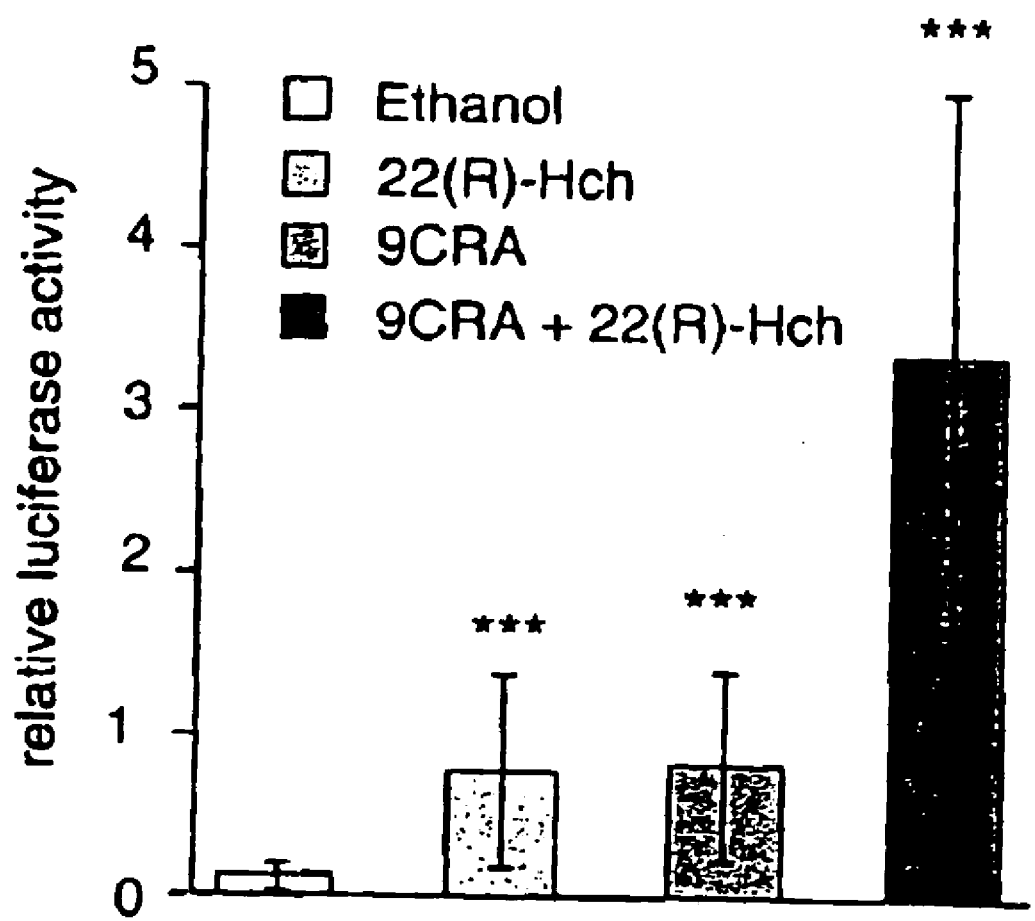
FIGS. 5A–5C show activation of the hABC1 promoter by oxysterols and retinoic acid in RAW 264.7 cell.
Figure 5B:
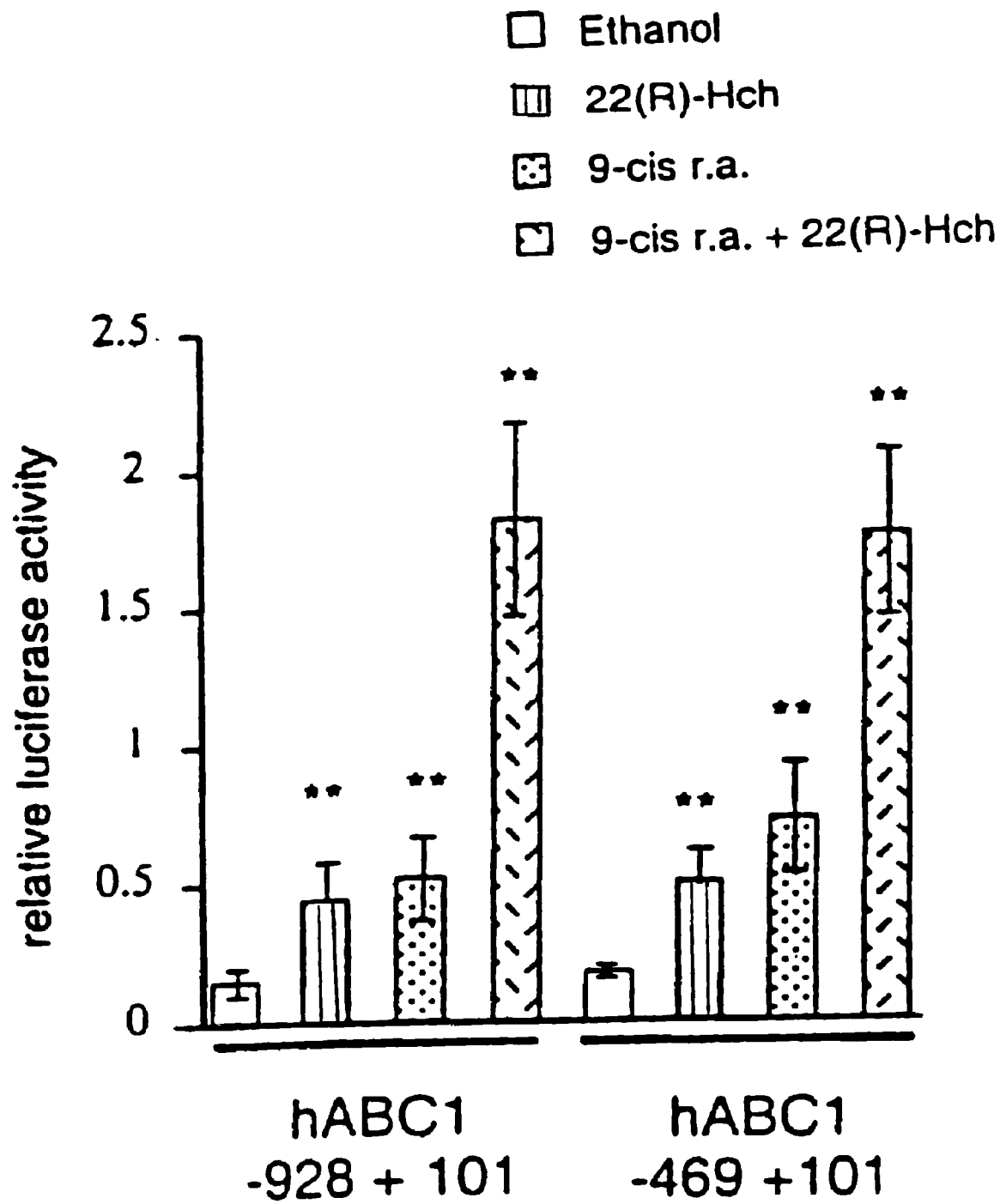

To investigate the function of the potential hABC1 promoter, we transfected the macrophage-like RAW 264.7 cell line with a promoter-luciferase construct (FIGS. 5A and 5B). We used 9CRA as an activator of endogenous RXR, and 22(R)-HCh, which is a good activator of LXR-RXR (33) and a poor activator of SF1 (24). Compared to basal conditions, transfected cells treated with 22(R)-HCh or 9CRA exhibit 7 fold and 8 fold higher promoter activity, respectively (P<0.001) (FIG. 5A). When both compounds are added together, there was a synergistic 37 fold induction (P<0.001). A similar response was obtained with promoter fragments containing 928 bp or 469 bp of upstream sequence (FIG. 5B).

Figure 5C:
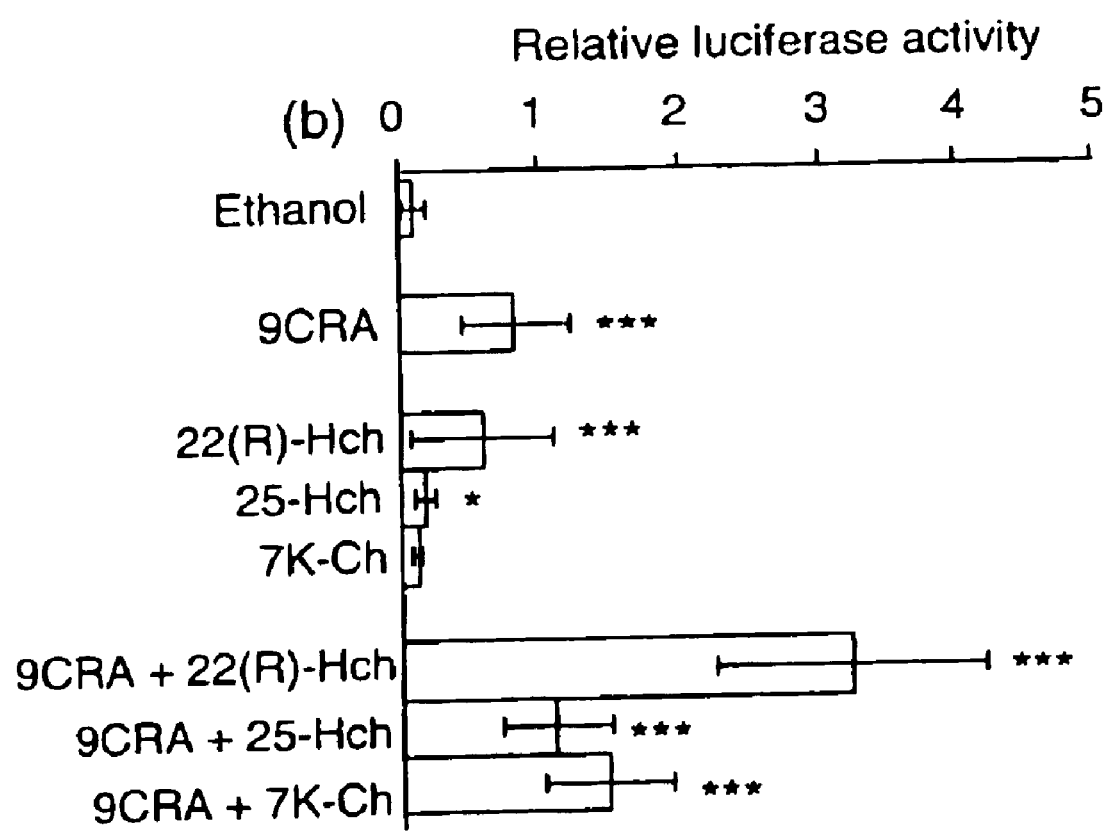

Next we compared the response of the ABC1 promoter to different sterols (FIG. 5C). We treated the transfected cells with 25-HCh which is a good activator of SF-1 and a poor activator of LXR (24). We also treated them with 7-KCh which is relatively abundant in human arterial foam cells (34). 25-HCh is a poor inducer of the hABC1 promoter compared to 22(R)-HCh (1.5 fold activation, P<0.05). No significant effect of 7-KCh was detected. However, when added in combination with 9CRA, a significant additive effect is detected for 7-KC (2 fold when compared to 9CRA alone, P<0.01). This pattern of sterol responsiveness is consistent with a transcriptional mechanism involving LXR.

LXRα and LXRβ are Both Expressed in Macrophages

Figure 4:
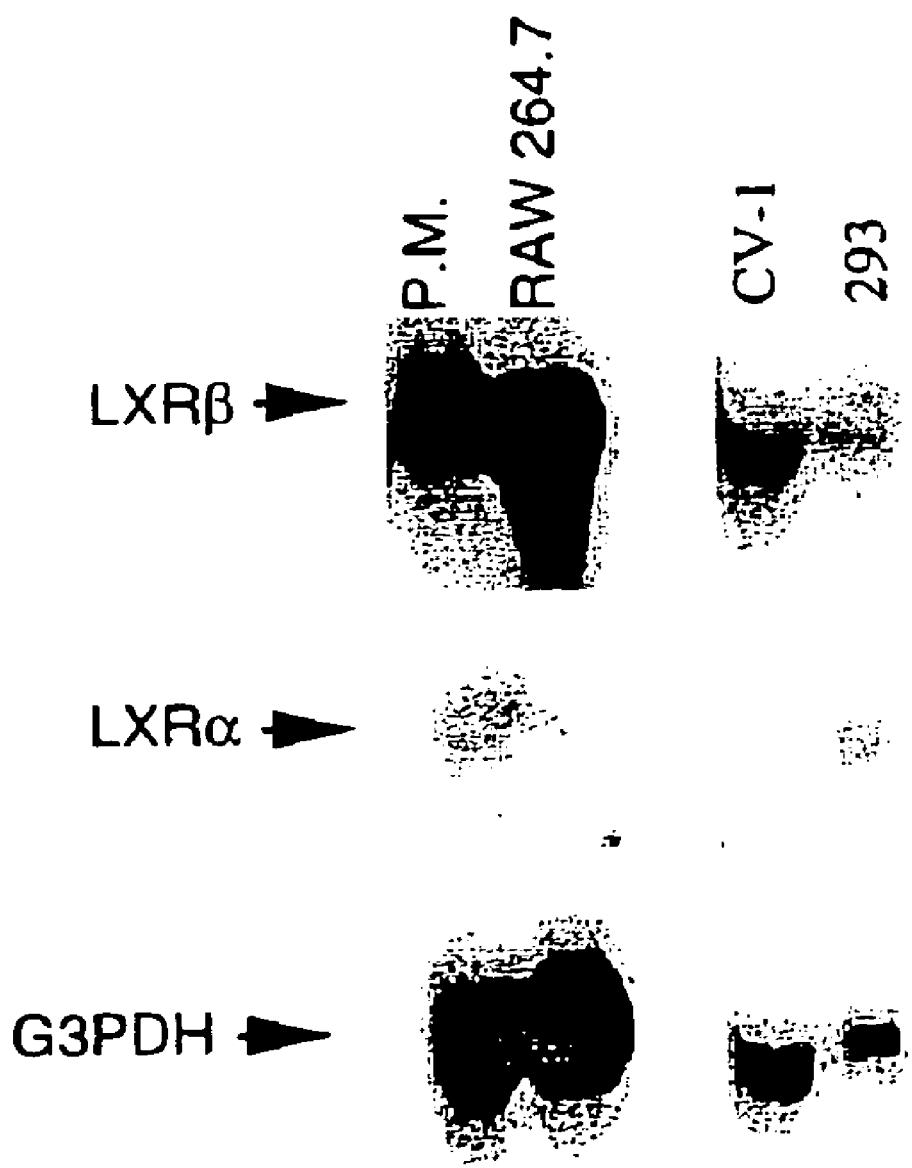
FIG. 4 shows the expression of LXRα and LXRβ in mouse peritoneal macrophages (PM), RAW 264.7 cells, 293 cells and CV-1 cells. Cells were isolated and cultured as described in "Material and methods". A Northern blot was performed with 35 µg of total RNA of each cell line. Hybridizations were performed using probes of similar specific activities, hLXRα, mLXRβ and mG3PDH as an internal standard.

To further investigate the potential role of LXRα and LXRβ in the upregulation of hABC1 we verified that the mRNAs of these nuclear receptors were present in RAW264.7 cells (FIG. 4). We also analysed their expression in vivo, using thioglycollate-elicited peritoneal macrophages from mice. Both receptors were detected in macrophages by Northern blot of total RNA, with a stronger signal for LXRβ. We also selected two cell lines for our transactivation experiments: CV-1 and 293 cells. As shown in FIG. 4, both LXRα and LXRβ could be detected in 293 cells, and LXRβ was detected in CV1 cells.

LXR/RXR Activates the hABC1 Promoter in 293 and CV-1 Cells.

Figure 6B:
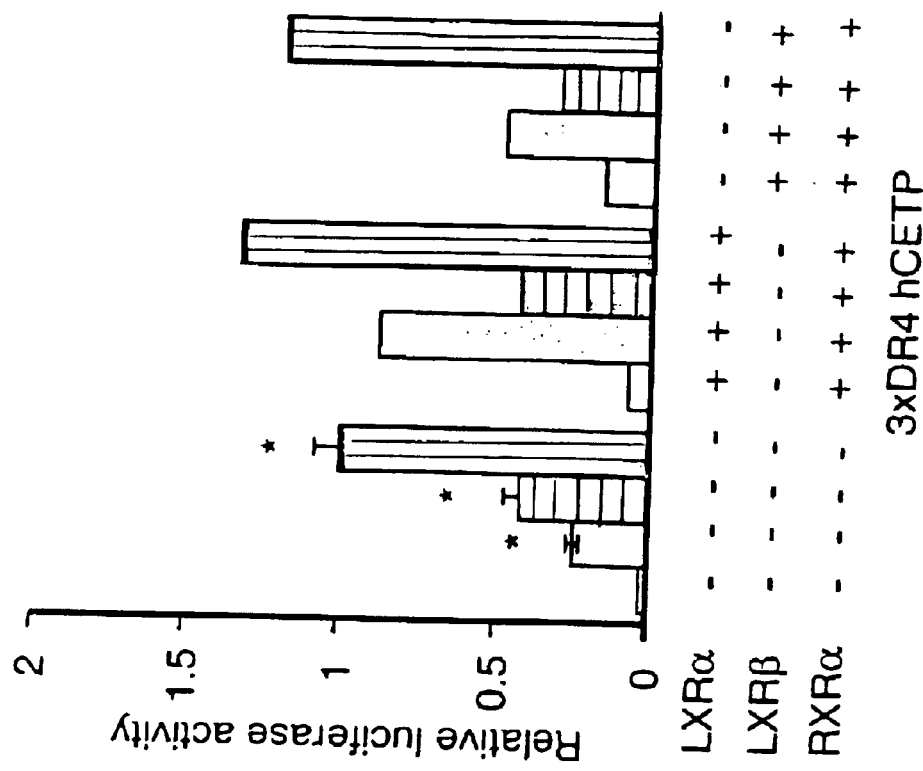
FIGS. 6A and 6B show Sterol and LXR/RXR activation of the hABC1 promoter in 293 cells.
Figure 6A:
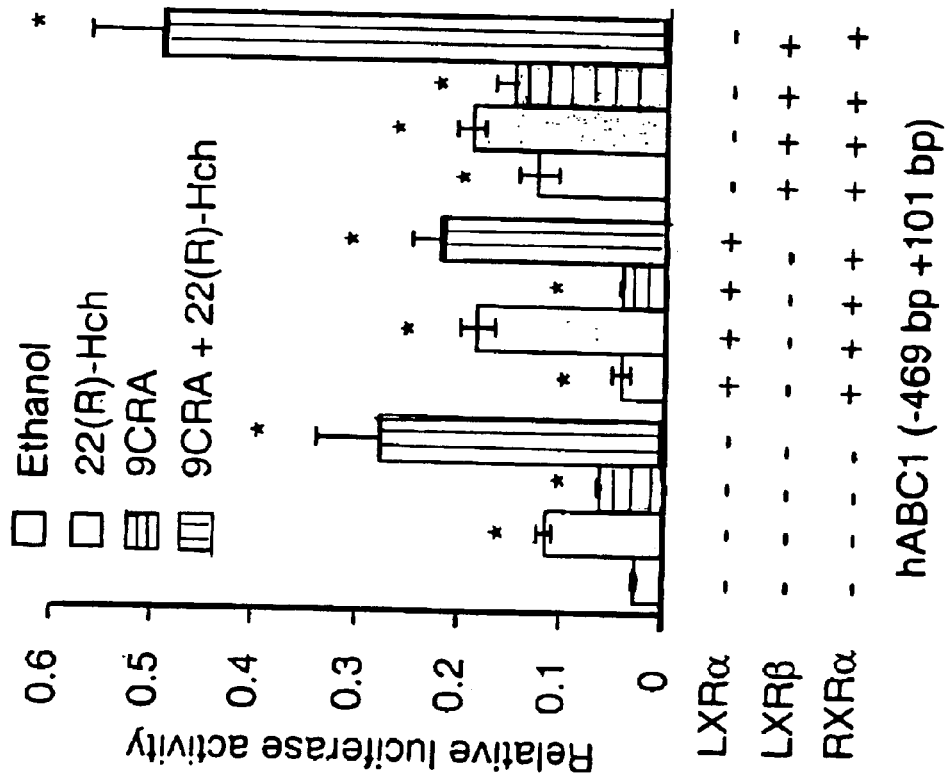
Figure 7:
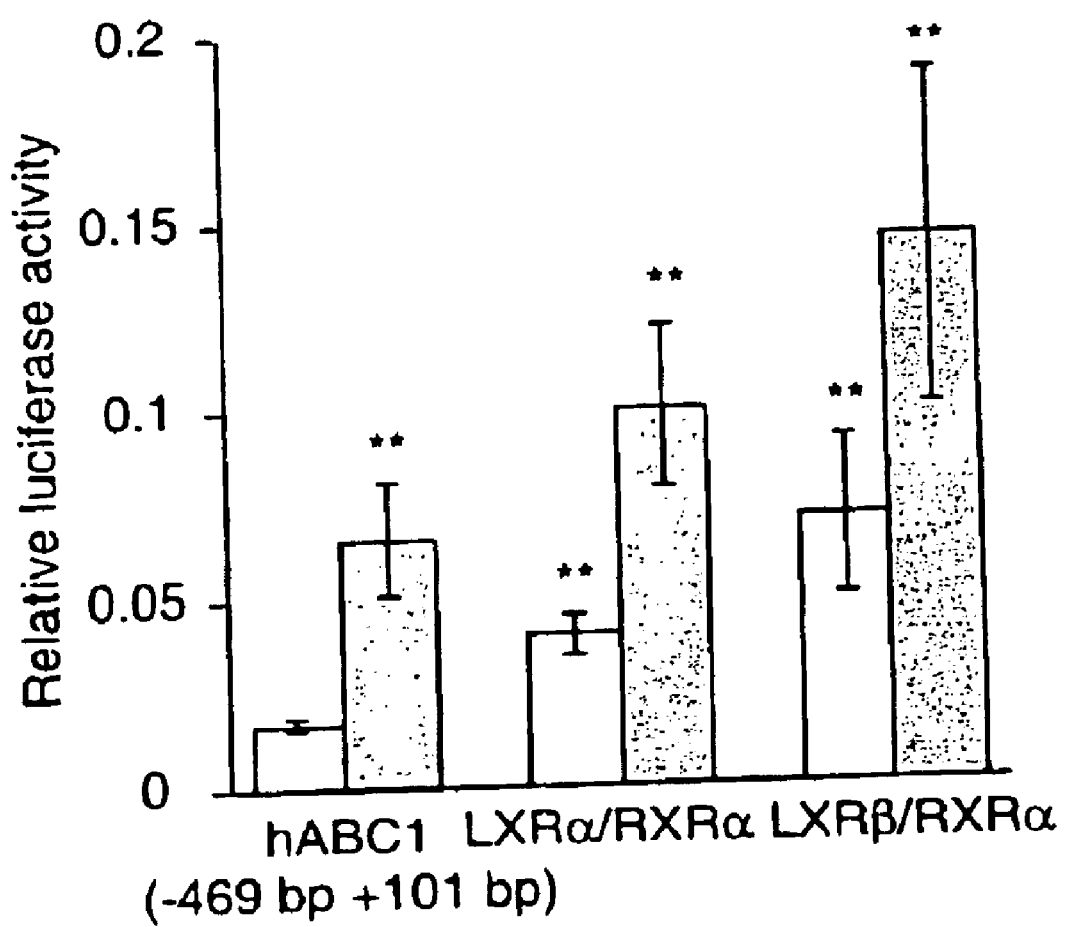
FIG. 7 shows transactivation of the hABC1 promoter by LXR/RXR in CV-1 cells. CV-1 cells were transfected and treated according to the protocols described in FIG. 5. Two to three independent experiments in duplicates were performed. Mann Withney tests analyse the difference between "Ethanol" and "Treatment". **=P<0.05.

In order to define the involvment of hRXRα and/or LXRα/β in the sterol upregulation of hABC1, we cotransfected 293 cells with the human ABC1 promoter and with these receptors (FIG. 6). We used a shorter promoter (deletion −460), which was sterol-responsive in macrophages (FIG. 5C). In 293 cells, without transfected LXR/hRXR, we obtained an upregulation of the promoter by 22-(R)-HCh-(4.5 fold, P<0.05) and 9CRA (3.5 fold, P<0.05) alone. The combination of 9CRA and 22(R)-HCh resulted in an additive effect (10 fold, P<0.05). When LXRα/hRXRα were transfected, basal activity was slightly increased (1.5 fold), as was the sterol response, but there was no additional effect of 9CRA or 9CRA+22(R)-HCh. However, transfection of LXRβ/RXRα caused a 5 fold increase in basal expression and a synergistic effect of 9CRA+22(R)-HCh (19 fold when compared to ethanol and 3 fold when compared to 9CRA alone, P<0.05).

As a positive control for these experiments we used a construct containing 3 copies of the LXR/hRXRα binding site of the CETP promoter (22). Even in the absence of transfected receptors, this construct is highly sterol and retinoic acid responsive in 293 cells (14 fold and 24 fold increase in luciferase activity, P<0.05) and an additive or synergistic effect (58 fold) is obtained with cotreatment. The LXR transfection experiments result increased basal activity and increased induction by sterols. However, 9CRA provide no further increase in activity compared to non-transfected cells. These results suggest that endogenous LXRs, in 293 cells, play a role in the response of both ABC1 and CETP promoters with a further increase in sterol-dependent promoter activity when LXR/RXR are transfected.

In CV-1 cells a significant sterol-activation of the promoter was detected without transfected receptors (4 fold, P<0.01). Cotransfection with hRXRα/LXRα or hRXRα/LXRβ increased the basal activity of the promoter (2 fold and 4 fold, both P<0.01). Exposure to 22(R)-HCh resulted in increased transactivation of the promoter (6 fold and 8 fold), compared to the control with no receptor.

Figure 8A:
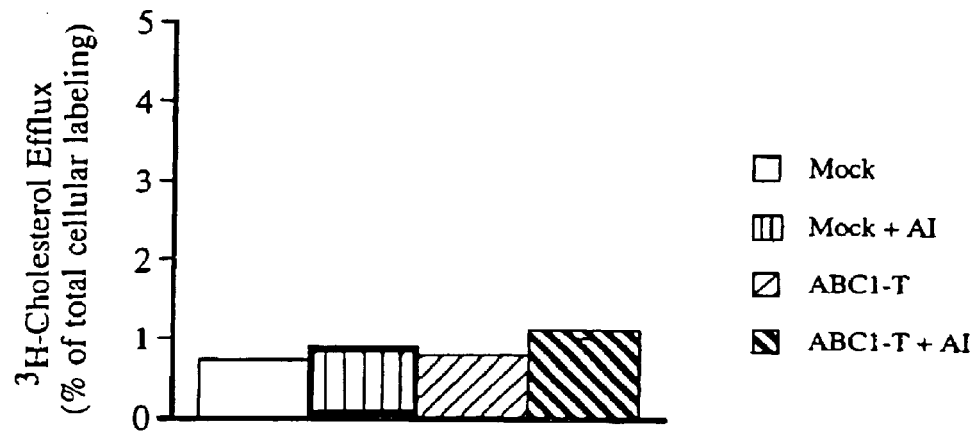
FIGS. 8A and 8B show expression studies showing that full length cDNA, including exons 1, 2, and 3 (FIG. 2) is active in promoting cholesterol efflux from cells while published cDNA is inactive. HEK 293 cells were plated in 12 well cell culture plates the day before transfection. Next day, cells about 95% confluence were transfected using Lipofectamine 2000 (GIBCO-BRL, MD) and corresponding plasmid constructs. The cells were labeled for 20 hours with $^3$H-cholestereol at 0.5 µCi/ml in DMEM media plus 10% FBS. Then, cells were washed 3 times with PBS and equilibrated in DMEM media plus 0.2% fatty free BSA for 3 hours. The media were replaced with fresh DMEM, 0.2% BSA media in the presence or absence of 10 µg/ml human apolipoprotein AI. After 6 hours incubation, the media and cells were separately collected and the cholesterol efflux was measured as a percentage of 3H-cholesterol efflux over total cellular labeling.
Figure 8B:
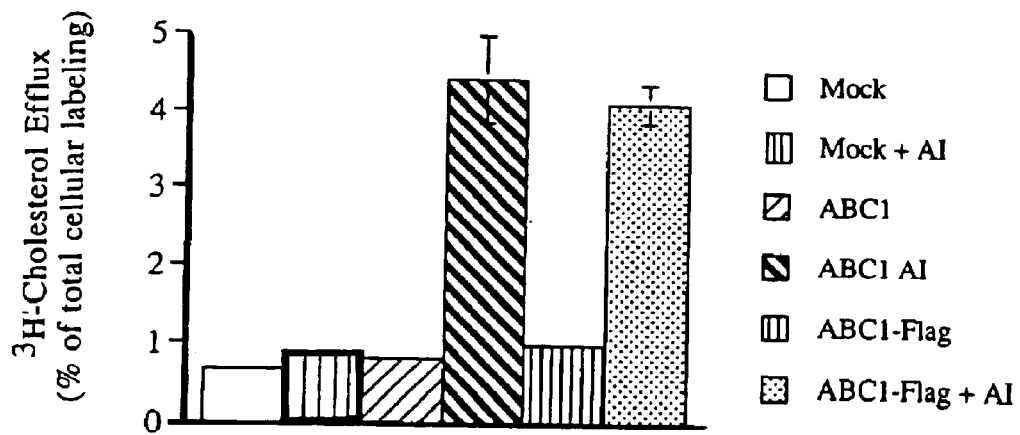

The full lenght form of the cDNA, incorporating exons 1–3 (FIG. 2A), was active in promoting cellular cholesterol efflux (FIG. 8B) while the shorter form, reported previously (8a, 8b, 9–12, 14) was inactive (FIG. 8A).

DISCUSSION

The described study has identified a region of the human ABC1 promoter, which is active in macrophages and is induced by 22 (R)-HCholesterol and 9-cis retinoic acid. The characterization of the major transcript in cholesterol-loaded THP1 macrophages led to the identification of this promoter, and also showed that most upstream ATG in the previously published cDNA (18) does not represent the authentic translation initiation site. Previous functional studies using this cDNA were describing the properties of a protein fragment truncated in the signal peptide, and we will need to be re-assessed with full length cDNA, as described herein. Our expression studies also verified that only the full length cDNA containing the new exons 1–3 (FIG. 2) was functionally active in promoting cellular cholesterol efflux (FIG. 8). The pattern of activation of the hABC1 promoter by specific oxysterols and 9CRA, as well as the transactivation experiments, strongly implicate LXR/RXR heterodimer in increasing transcription of the ABC1 gene. Thus, LXR and/or RXR agonists could be useful drugs to reverse foam cell formation and atherogenesis.

The mechanism of upregulation of ABC1 by acLDL (18) has not been studied. Our results with promoter-reporter constructs implicate a transcriptional mechanism. The 928bp fragment of promoter we cloned is sufficient for a basal expression of ABC1 in macrophages and its upregulation by oxysterols and retinoic acid, separately or synergisticaly. Several lines of evidence indicate a a role for LXRs in the sterol-mediated activation of hABC1: 1) 22(R) hydroxycholesterol or 25-HCh and 9CRA activate the hABC1 promoter alone or in a synergistic fashion (25, 29), 2) 22(R)hydroxycholesterol is a more potent inducer than 25-HCh, in accordance with the literature (33) and different to the characteristics of the activation of another oxysterol-activated nuclear receptor, SF1 (24), 3)LXR$\beta$ and LXR$\alpha$ are endogenously expressed in RAW264.7 cells, in thioglycollate-elicited peritoneal macrophages and in fresh human monoyte-derived macrophages (Yu Sun and A. Tall, unpublished results), 4)LXR$\beta$/hRXR$\alpha$, and to a lesser extent LXR$\alpha$/hRXR$\alpha$, activate the ABC1 promoter when cotransfected in CV-1 and 293 cells.

The pattern of activation of the ABC1 promoter by sterols suggests that its expression may be suboptimal in atherosclerotic lesions. Thus, 7-KCh is relatively abundant in oxidized-LDL and in atheroma foam cells (37), and is a poor activator of the hABC1 promoter (FIG. 5C). 27-HCh, also abundant in foam cells, is a relatively poor activator of LXR (32,36). Thus, the accumulation of oxysterols in atherosclerotic lesions probably does not result in optimal activation of hABC1. This suggests that small molecules that are optimal LXR activators might be effective drugs at reversing foam cell information, and that they might be useful as a treatment for atherosclerosis. The activation of the hABC1 promoter by 9CRA is increased 2 fold when given with 7-KCh (FIG. 5C). This further suggests that, with regard to the induction of ABC1 by oxysterols, an unfavorable foam cell environment could also be switched to a more favorable one by delivery of ligands for RXR.

The inability of LXR$\beta$ to compensate for the lack of LXR$\alpha$ in -LXR$\alpha$-/- mice (21) suggests that these receptors have different targets. In vitro, both LXR$\alpha$ and LXR$\beta$ are able to upregulate hABC1 (FIGS. 5 and 6) or CETP (22), but LXR$\beta$ is clearly more effective than LXR$\alpha$ in mediating the sterol response of ABC1. This also is consistent with the fact that LXR$\beta$ appears to be more highly expressed than LXR$\alpha$ in macrophages (FIG. 5).

The hABC1 promoter contains several potentially interesting transcription factor binding sites (FIG. 3). A CREBP1-CJUN element, at –1039, could be responsible for the upregulation of ABC1 by cAMP obtained in human fibroblasts (8). Atherosclerosis involves inflammatory processes (35). In foam cells, the efflux of cholesterol is down regulated and its trafficking modified by interferon gamma (36). ABC1 has also been implicated in the secretion of the proinflammatory cytokine Il-$1_B$ (37). Macrophages and fibroblasts treated with Il-$1_B$ exhibit a makedly increase of cholesterol efflux to lipid-free apolipoprotein AI (38). Therefore it is interesting to note several potential binding sites for transcription factors such as Nuclear Factor Kappa B or AP-1, mediators of the Il-$1_B$ response (39). These factors have also been implicated in the response to oxidized LDL, but are probably not involved in the induction of hABC1 mRNA by oxysterols, since the truncated promoter, lacking these sites was equally as active as the longer promoter (FIG. 5B).

The results of the 5'RACE PCR suggest that the hABC1 gene can be spliced into different transcripts. Whether this splicing has a physiologicaly significant role is not known. It seems that the cholesterol loading of macrophages results in the synthesis of one major transcript, also present in HEPG2 cells among a more heterogenous hABC1 mRNA population. Every transcript we found possesses a start codon upstream of exon 4 wich excludes the previously published start codon (11) and rather makes exon 4 a good candidate for the signal peptide. Because mRNAs starting from exon 3 are present in HEPG2 cells, we cannot exclude the presence of one or two other active promoters, upstream of exon 2 and 3.

To conclude, we have shown that hABC1 is upregulated at a transcriptionnal level by oxysterols and 9CRA through a DNA element located between –469 bp to +101 bp (FIG. 2). This activation is likely to involve the nuclear hormone receptor LXR$\beta$/RXR but further studies will be needed to show whether this is a direct effect on the promoter, or is mediated by an indirect mechanism. Although the relevant region of the hABC1 promoter does not contain an obvious LXR binding region, such sequences can be occult (22). These results provide strong support for the idea that LXRs may help to coordinate different steps in reverse cholesterol transport (22). For example, CETP activity results in the remodeling of HDL into small particles and liberates free apoA-I from HDL (40). Small HDL and free apoA-I appear to be the optimal substrates for ABC1 (41). Thus, coordinate induction of CETP and ABC1 by LXR$\beta$/RXR might act synergistically to enhance cholesterol efflux from macrophage foam cells.

REFERENCES

6. Castelli, W. P., Garrison, R. J., Wilson, P. W., Abbott, R. D., Kalousdian, S., and Kannel, W. B. (1986) *Jama* 256(20), 2835–8
7. Serfaty-Lacrosniere, C., Civeira, F., Lanzberg, A., Isaia, P., Berg, J., Janus, E. D., Smith, M. P., Jr., Pritchard, P. H., Frohlich, J., Lees, R. S., and et al. (1994) *Atherosclerosis* 107(1), 85–98
8. Marcil, M., Brooks-Wilson, A., Clee, S. M., Roomp, K., Zhang, L. H., Yu, L., Collins, J. A., van Dam, M., Molhuizen, H. O., Loubster, O., Ouellette, B. F., Sensen, C. W., Fichter, K., Mott, S., Denis, M., Boucher, B., Pimstone, S., Genest, J., Jr., Kastelein, J. J., and Hayden, M. R. (1999) *Lancet* 354(9187), 1341–6
9. Bruce, C., Chouinard, R. A., Jr., and Tall, A. R. (1998) *Annu Rev Nutr* 18, 297–330
10. Rothblat, G. H., de la Llera-Moya, M., Atger, V., Kellner-Weibel, G., Williams, D. L., and Phillips, M. C. (1999) *J Lipid Res* 40(5), 781–96
11. Remaley, A. T., Schumacher, U. K., Stonik, J. A., Farsi, B. D., Nazih, H., and Brewer, H. B., Jr. (1997) *Arterioscler Thromb Vasc Biol* 17(9), 1813–21
12. Marcil, M., Yu, L., Krimbou, L., Boucher, B., Oram, J. F., Cohn, J. S., and Genest, J., Jr. (1999) *Arterioscler Thromb Vasc Biol* 19(1), 159–69

8a. Lawn, R. M., Wade, D. P., Garvin, M. R., Wang, X., Schwartz, K., Porter, J. G., Seilhamer, J. J., Vaughan, A. M., and Oram, J. F. (1999) *J Clin Invest* 104(8), R25–31

8b. Bodzioch, M., Orso, E., Klucken, J., Langmann, T., Bottcher, A., Diederich, W., Drobnik, W., Barlage, S., Buchler, C., Porsch-Ozcurumez, M., Kaminski, W. E., Hahmann, H. W., Oette, K., Rothe, G., Aslanidis, C., Lackner, K. J., and Schmitz, G. (1999) *Nat Genet* 22(4), 347–51

13. Rust, S., Walter, M., Funke, H., von Eckardstein, A., Cullen, P., Kroes, H. Y., Hordijk, R., Geisel, J., Kastelein, J., Molhuizen, H. O., Schreiner, M., Mischke, A., Hahmann, H. W., and Assmann, G. (1998) *Nat Genet* 20(1), 96–8

11. Remaley, A. T., Rust, S., Rosier, M., Knapper, C., Naudin, L., Broccardo, C., Peterson, K. M., Koch, C., Arnould, I., Prades, C., Duverger, N., Funke, H., Assman, G., Dinger, M., Dean, M., Chimini, G., Santamarina-Fojo, S., Fredrickson, D. S., Denefle, P., and Brewer, H. B., Jr. (1999) *Proc Natl Acad Sci USA* 96(22), 12685–90

12. Brooks-Wilson, A., Marcil, M., Clee, S. M., Zhang, L. H., Roomp, K., van Dam, M., Yu, L., Brewer, C., Collins, J. A., Molhuizen, H. O., Loubser, O., Ouelette, B. F., Fichter, K., Ashbourne-Excoffon, K. J., Sensen, C. W., Scherer, S., Mott, S., Denis, M., Martindale, D., Frohlich, J., Morgan, K., Koop, B., Pimstone, S., Kastelein, J. J., Hayden, M. R., and et al. (1999) *Nat Genet* 22(4), 336–45

13. Brousseau, M. E., Schaefer, E. J., Dupuis, J., Eustace, B., Van Eerdewegh, P., Goldkamp, A. L., Thurston, L. M., FitzGerald, M. G., Yasek-McKenna, D., O'Neill, G., Eberhart, G. P., Weiffenbach, B., Ordovas, J. M., Freeman, M. W., Brown, R. H., Jr., and Gu, J. Z. (2000) *J Lipid Res* 41(3), 433–441

14. Orso, E., Broccardo, C., Kaminski, W. E., Bottcher, A., Liebisch, G., Drobnik, W., Gotz, A., Chambenoit, O., Diederich, W., Langmann, T., Spruss, T., Luciani, M. F., Rothe, G., Lackner, K. J., Chimini, G., and Schmitz, G. (2000) *Nat Genet* 24(2), 192–6

15. Croop, J. M. (1998) *Methods Enzymol* 292, 101–16

16. Broccardo, C., Luciani, M., and Chimini, G. (1999) *Biochim Biophys Acta* 1461(2), 395–404

17. Luciani, M. F., Denizot, F., Savary, S., Mattei, M. G., and Chimini, G. (1994) *Genomics* 21(1), 150–9

18. Langmann, T., Klucken, J., Reil, M., Liebisch, G., Luciani, M. F., Chimini, G., Kaminski, W. E., and Schmitz, G. (1999) *Biochem Biophys Res Commun* 257 (1), 29–33

19. Klucken, J., Buchler, C., Orso, E., Kaminski, W. E., Porsch-Ozcurumez, M., Liebisch, G., Kapinsky, M., Diederich, W., Drobnik, W., Dean, M., Allikmets, R., and Schmitz, G. (2000) *Proc Natl Acad Sci USA* 97(2), 817–22

20. Brown, M. S., and Goldstein, J. L. (1997) *Cell* 89(3), 331–40

21. Peet, D. J., Turley, S. D., Ma, W., Janowski, B. A., Lobaccaro, J. M., Hammer, R. E., and Mangelsdorf, D. J. (1998) *Cell* 93(5), 693–704

22. Luo, Y., and Tall, A. R. (2000) *J Clin Invest* 105(4), 513–20

23. Christenson, L. K., McAllister, J. M., Martin, K. O., Javitt, N. B., Osborne, T. F., and Strauss, J. F., 3rd. (1998) *J Biol Chem* 273(46), 30729–35

24. Lala, D. S., Syka, P. M., Lazarchik, S. B., Mangelsdorf, D. J., Parker, K. L., and Heyman, R. A. (1997) *Proc Natl Acad Sci USA* 94(10), 4895–900

25. Willy, P. J., Umesono, K., Ong, E. S., Evans, R. M., Heyman, R. A., and Mangelsdorf, D. J. (1995) *Genes Dev* 9(9), 1033–45

26. Teboul, M., Enmark, E., Li, Q., Wikstrom, A. C., Pelto-Huikko, M., and Gustafsson, J. A. (1995) *Proc Natl Acad Sci USA* 92(6), 2096–100

27. Feltkamp, D., Wiebel, F. F., Alberti, S., and Gustafsson, J. A. (1999) *J Biol Chem* 274(15), 10421–9

28. Song, C., Kokontis, J. M., Hiipakka, R. A., and Liao, S. (1994) *Proc Natl Acad Sci USA* 91(23), 10809–13

29. Janowski, B. A., Willy, P. J., Devi, T. R., Falck, J. R., and Mangelsdorf, D. J. (1996) *Nature* 393(6602), 728–31

30. Sambrook, J., Fritsch, E. F., and Maniatis, T. (1989) *molecular cloning: A Laboratory Manual,* 2nd Ed., Cold Spring Harbor Laboratory, Cold Spring Harbor, N.Y.

31. Shipley, J. M., Wesselschmidt, R. L., Kobayashi, D. K., Ley, T. J., and Shapiro, S. D. (1996) *Proc Matl Acad Sci USA* 93(9), 3942–6

32. Seol, W., Choi, H. S., and Moore, D. D. (1995) *Mol Endocrinol* 9(1), 72–85

33. Lehmann, J. M., Kliewer, S. A., Moore, L. B., Smith-Oliver, T. A., Oliver, B. B., Su, J. L., Sundseth, S. S., Winegar, D. A., Blanchard, D. E., Spencer, T. A., and Willson, T. M. (1997) *J Biol Chem* 272(6), 3137–40

34. Hulten, L. M., Lindmark, H., Diczfalusy, U., Bjorkhem, I., Ottosson, M., Liu, Y., Bondjers, G., and Wiklund, O. (1996) *J Clin Invest* 97(2), 461–8

35. Ross, R. (1999) *N Engl J Med* 340(2), 115–26

36. Panousis, C. G., and Zuckerman, S. H. (2000) *J Lipid Res* 41(1), 75–83

37. Hamon, Y., Luciani, M. F., Becq, F., Verrier, B., Rubartelli, A., and Chimini, G. (1997) *Blood* 90(8), 2911–5

38. Kronqvist, R., Leppimaki, P., Mehto, P., and Slotte, J. P. (1999) *Eur J Biochem* 262(3), 939–46

39. Ohlsson, B. G., Englund, M. C., Karlsson, A. L., Knutsen, E., Erixon, C., Skribeck, H., Liu, Y., Bondjers, G., and Wiklund, O. (1996) *J Clin Invest* 98(1), 78–89

40. Rye, K. A., Hime, N. J., and Barter, P. J. (1997) *J Biol Chem* 272 (7), 3953–60

41. Scott, J. (1999) *Nature* 400(6747), 816–7, 819

What is claimed is:

1. An isolated human ABC1 promoter that directs transcription of a heterologous coding sequence positioned downstream therefrom, wherein the promoter is selected from the group consisting of:
   (a) a promoter comprising nucleotides having the nucleotide sequence shown in SEQ ID NO: 1;
   (b) a promoter comprising nucleotides having the nucleotide sequence beginning a bp 624 and ending at bp 1197 of SEQ ID NO: 1; and
   (c) a promoter comprising nucleotides having the nucleotide sequence beginning at bp 1005 and ending at bp 1059 of SEQ ID NO: 1.

2. The promoter of claim 1, wherein the promoter comprises the nucleotide sequence shown in SEQ ID NO: 1.

3. A recombinant expression construct effective in directing the transcription of a selected coding sequence which comprises:
   (a) a human ABC1 promoter nucleotide sequence according to claim 1; and
   (b) a coding sequence operably linked to the promoter, whereby the coding sequence can be transcribed and translated in a host cell, and the promoter is heterologous to the coding sequence.

4. The recombinant expression construct of claim 3, wherein the coding sequence encodes a transporter polypeptide.

5. The recombinant expression construct of claim 4, wherein the transported polypeptide is ABCA1 transmembrane transporter protein.

6. The recombinant expression construct of claim 4, further comprising a nucleic acid segment encoding a transactivator protein that upregulates the ABC1 promoter.

7. The recombinant expression construct of claim 6, wherein the transactivator protein is the Liver-X-Receptor, the Retinoid-X-Receptor, or a heterodimer of the Liver-X-Receptor and the Retinoid-X-Receptor.

8. A host cell in cell culture comprising the recombinant expression construct of claim 3.

9. The host cell of claim 8, wherein the host cell is stably transformed with the recombinant expression construct.

10. The host cell of claim 8, wherein the host cell is a macrophage.

11. The host cell of claim 8, wherein the host cell is an immortalized cell.

12. The host cell of claim 8, wherein the cell is selected from the group consisting of RAW cells, African green monkey CV-1 cells and human 293 cells.

13. A method for expressing a foreign DNA in a host cell in cell culture comprising: introducing into the host cell in cell culture a gene transfer vector comprising the ABC1 promoter according to claim 1 operably linked to the foreign DNA encoding a desired polypeptide or RNA, wherein said foreign DNA is expressed.

14. The method of claim 13, wherein the promoter nucleotide sequence is identical to the sequence set forth in SEQ ID NO: 1.

15. The method of claim 13, wherein the gene transfer vector encodes and expresses a reporter molecule.

16. The method of claim 15, wherein the reporter molecule is selected from the group consisting of beta-galactosidase, beta-glucuronidase, luciferase, chloramphenicol acetyltransferase, neomycin phosphotransferase, and guanine xanthine phosphoribosyltransferase.

17. The method of claim 13, wherein the introducing is carried but by adenovirus infection, liposome-mediated-transfer, topical application to the cell, or microinjection.

18. The method of claim 13, further comprising introducing into the cell a gene transfer vector comprising a nucleic acid segment encoding a transactivator protein capable of upregulating the ABC1 promoter.

19. The method of claim 18, wherein the transactivator protein is the Liver-X-Receptor, the Retinoid-X-Receptor, or a heterodimer of the Liver-X-Receptor and the Retinoid-X-Receptor.

20. The method of claim 13, further comprising contacting the cell with a transactivator protein capable of upregulating the ABC1 promoter.

21. The method of claim 20, wherein the transactivator protein is the Liver-X-Receptor, the Retinoid-X-Receptor, or a heterodimer of the Liver-X-Receptor and the Retinoid-X-Receptor.

22. The method of claim 21, further comprising contacting the cell with an agonist of the Liver-X-Receptor, of the Retinoid-X-Receptor, or of a heterodimer of the Liver-X-Receptor and the Retinoid-X-Receptor.

23. The isolated promoter of claim 1, wherein the promoter comprises nucleotides having the nucleotide sequence beginning at bp 1005 and ending at bp 1059 of SEQ ID NO: 1.

24. A recombinant expression construct which comprises the nucleic acid according to claim 23.

* * * * *

SEQUENCE LISTING

<160> NUMBER OF SEQ ID NOS: 17

<210> SEQ ID NO 1
<211> LENGTH: 1197
<212> TYPE: DNA
<213> ORGANISM: human

```
<400> SEQUENCE: 1
acctgagttt tggccagaat aagtgacat  ttagtttgtt ggcttgatgg atgacttaaa     60
tatttagaca tatggtgtgt aggcctgcat tcctactctt gccttttttt ttgcccctcc    120
agtgttttgg gtagttttgc tcccctacag ccaaaggcaa acagataagt tggaggtctg    180
gagtggctac ataattttac acgactgcaa ttctctggct gcacttcaca aatgtataca    240
aactaaatac aagtcctgtg tttttatcac agggaggctg atcaatataa tgaaattaaa    300 aggggggctgg tccatattgt tctgtgtttt tgtttgtttg tttctttttt tgtttttgtg    360
gcctccttcc tctcaattta tgaagagaag cagtaagatg ttcctctcgg gtcctctgag    420
ggacctgggg agctcaggct gggaatctcc aaggcagtag gtcgcctatc aaaaatcaaa    480
gtccaggttt gtgggggggaa aacaaaagca gcccattacc cagaggactg tccgccttcc    540
cctcacccca gcctaggcct ttgaaaggaa acaaaagaca agacaaaatg attggcgtcc    600
tgagggagat tcagcctaga gctctctctc cccaatccct ccctccggct gaggaaacta    660
acaaaggaaa aaaaaattgc ggaaagcagg atttagagga agcaaattcc actggtgccc    720
ttggctgccg ggaacgtgga ctagagagtc tgcggcgcag ccccgagccc agcgcttccc    780
gcgcgtctta ggccggcggg cccgggcggg ggaagggac gcagaccgcg gaccctaaga    840
cacctgctgt accctccacc cccaccccac ccacctcccc ccaactccct agatgtgtcg    900
tgggcggctg aacgtcgccc gtttaagggg cgggccccgg ctccacgtgc tttctgctga    960
gtgactgaac tacataaaca gaggccggga acggggcggg gaggagggag agcacaggct   1020
ttgaccgata gtaacctctg cgctcggtgc agccgaatct ataaaaggaa ctagtcccgg   1080
caaaaacccc gtaattgcga gcgagagtga gtggggccgg gacccgcaga gccgagccga   1140
cccttctctc ccgggctgcg gcagggcagg gcggggagct ccgcgcacca acagagc      1197

<210> SEQ ID NO 2
<211> LENGTH: 61
<212> TYPE: PRT
<213> ORGANISM: human

<400> SEQUENCE: 2

Met Ala Cys Trp Pro Gln Leu Arg Val Leu Leu Trp Lys Asn Leu Thr
1               5                   10                  15

Phe Arg Arg Arg Gln Thr Cys Gln Leu Leu Glu Val Ala Trp Pro
            20                  25                  30

Leu Phe Ile Phe Leu Ile Leu Ile Ser Val Arg Leu Ser Tyr Pro Pro
        35                  40                  45

Tyr Glu Gln His Glu Cys His Phe Pro Asn Lys Ala Met
    50                  55                  60

<210> SEQ ID NO 3
<211> LENGTH: 40
<212> TYPE: PRT
<213> ORGANISM: human

<400> SEQUENCE: 3

Met Cys Gln Leu Leu Leu Glu Val Ala Trp Pro Leu Phe Ile Phe Leu
1               5                   10                  15

Ile Leu Ile Ser Val Arg Leu Ser Tyr Pro Pro Tyr Glu Gln His Glu
            20                  25                  30

Cys His Phe Pro Asn Lys Ala Met
        35                  40
```

```
<210> SEQ ID NO 4
<211> LENGTH: 56
<212> TYPE: PRT
<213> ORGANISM: human

<400> SEQUENCE: 4

Gln Leu Arg Val Leu Leu Trp Lys Asn Leu Thr Phe Arg Arg Gln
1               5                   10                  15

Thr Cys Gln Leu Leu Glu Val Ala Trp Pro Leu Phe Ile Phe Leu
            20                  25                  30

Ile Leu Ile Ser Val Arg Leu Ser Tyr Pro Pro Tyr Glu Gln His Glu
        35                  40                  45

Cys His Phe Pro Asn Lys Ala Met
    50                  55

<210> SEQ ID NO 5
<211> LENGTH: 44
<212> TYPE: PRT
<213> ORGANISM: human

<400> SEQUENCE: 5

Met Ala Cys Trp Pro Gln Leu Arg Val Leu Trp Lys Asn Leu Thr
1               5                   10                  15

Phe Arg Arg Arg Gln Thr Cys Gln Leu Leu Leu Glu Val Ala Trp Pro
            20                  25                  30

Leu Phe Ile Phe Leu Ile Leu Ile Ser Val Arg Leu
        35                  40

<210> SEQ ID NO 6
<211> LENGTH: 55
<212> TYPE: PRT
<213> ORGANISM: rat

<400> SEQUENCE: 6

Gln Ile Gln Leu Leu Trp Lys Asn Trp Thr Leu Arg Lys Arg Gln Lys
1               5                   10                  15

Ile Arg Phe Val Val Glu Leu Val Trp Pro Leu Ser Leu Phe Leu Val
            20                  25                  30

Leu Ile Trp Leu Arg Asn Ala Asn Pro Leu Tyr Ser His His Glu Cys
        35                  40                  45

His Phe Pro Asn Lys Ala Met
    50                  55

<210> SEQ ID NO 7
<211> LENGTH: 44
<212> TYPE: PRT
<213> ORGANISM: human

<400> SEQUENCE: 7

Met Ala Val Leu Arg Gln Leu Ala Leu Leu Trp Lys Asn Tyr Thr
1               5                   10                  15

Leu Gln Lys Arg Lys Val Leu Val Thr Val Leu Glu Leu Phe Leu Pro
            20                  25                  30

Leu Leu Phe Ser Gly Ile Leu Ile Trp Leu Arg Leu
        35                  40

<210> SEQ ID NO 8
<211> LENGTH: 28
<212> TYPE: DNA
<213> ORGANISM: human
```

-continued

```
<400> SEQUENCE: 8 cccctccct cgggatgccc gcagacaa                               28

<210> SEQ ID NO 9
<211> LENGTH: 24
<212> TYPE: DNA
<213> ORGANISM: human

<400> SEQUENCE: 9
gcctccgagc atctgagaac aggc                                  24

<210> SEQ ID NO 10
<211> LENGTH: 24
<212> TYPE: DNA
<213> ORGANISM: human

<400> SEQUENCE: 10
taattgcgag cgagagtgag tggg                                  24

<210> SEQ ID NO 11
<211> LENGTH: 22
<212> TYPE: DNA
<213> ORGANISM: human

<400> SEQUENCE: 11
cctacccctt gacaagcctt cc                                    22

<210> SEQ ID NO 12
<211> LENGTH: 29
<212> TYPE: DNA
<213> ORGANISM: human

<400> SEQUENCE: 12
ggttgtgtgt atttagcaca gcaggttgg                             29

<210> SEQ ID NO 13
<211> LENGTH: 29
<212> TYPE: DNA
<213> ORGANISM: human

<400> SEQUENCE: 13
tgcttcctat cgtgctttat ctggttcac                             29

<210> SEQ ID NO 14
<211> LENGTH: 26
<212> TYPE: DNA
<213> ORGANISM: human

<400> SEQUENCE: 14
aggtggcctg gcctctattt atcttc                                26

<210> SEQ ID NO 15
<211> LENGTH: 24
<212> TYPE: DNA
<213> ORGANISM: human

<400> SEQUENCE: 15
gcctccgagc atctgagaac aggc                                  24

<210> SEQ ID NO 16
<211> LENGTH: 20
<212> TYPE: DNA
```

```
-continued

<213> ORGANISM: human

<400> SEQUENCE: 16
accacagtcc atgccatcac                                                    20

<210> SEQ ID NO 17
<211> LENGTH: 20
<212> TYPE: DNA
<213> ORGANISM: human

<400> SEQUENCE: 17
tccaccaccc tgttgctgta                                                    20
```